United States Patent
Horita

(10) Patent No.: US 11,972,550 B2
(45) Date of Patent: Apr. 30, 2024

(54) IMAGE PROCESSING APPARATUS AND IMAGE PROCESSING METHOD

(71) Applicant: FUJIFILM Corporation, Tokyo (JP)

(72) Inventor: Shuhei Horita, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 852 days.

(21) Appl. No.: 16/935,988

(22) Filed: Jul. 22, 2020

(65) Prior Publication Data
US 2020/0349695 A1 Nov. 5, 2020

Related U.S. Application Data

(63) Continuation of application No. PCT/JP2018/048178, filed on Dec. 27, 2018.

(30) Foreign Application Priority Data

Feb. 2, 2018 (JP) ................. 2018-017280

(51) Int. Cl.
*G06T 7/00* (2017.01)
*G01N 21/88* (2006.01)
(Continued)

(52) U.S. Cl.
CPC ....... *G06T 7/0004* (2013.01); *G01N 21/8851* (2013.01); *G01N 21/892* (2013.01);
(Continued)

(58) Field of Classification Search
CPC . G06T 7/0004; G06T 7/0002; G06T 2200/24; G06T 2207/20081;
(Continued)

(56) References Cited

U.S. PATENT DOCUMENTS 9,036,861 B2 * 5/2015 Chen .................... G06T 7/0002
382/100
10,620,131 B2 4/2020 Kondo et al.
(Continued)

FOREIGN PATENT DOCUMENTS

EP 3 086 286 A1 10/2016
EP 3 483 594 A1 5/2019
(Continued)

OTHER PUBLICATIONS

An Office Action; "Notice of Reasons for Refusal", mailed by the Japanese Patent Office dated Sep. 17, 2021, which corresponds to Japanese Patent Application No. 2019-568946 and is related to U.S. Appl. No. 16/935,988; with English language translation.
(Continued)

*Primary Examiner* — Mischita L Henson
(74) *Attorney, Agent, or Firm* — Studebaker & Brackett PC

(57) ABSTRACT

According to an aspect of the invention, among the individual images, a detection result for the check target image for which it is determined that a user is encouraged to check the detection result or a detection result for the partial image acquired by cutting a partial region from the check target image is displayed on the display device to encourage the user to check the detection result, and the detection result is revised on the basis of an instruction input by the user. Therefore, the image for which the detection result is to be checked is distinctively displayed, and the detection result for the image is revised on the basis of an instruction input by the user, which results in reduction in the time taken for checking and revision.

26 Claims, 33 Drawing Sheets

(51) Int. Cl.
*G01N 21/892* (2006.01)
*G01N 21/95* (2006.01)
*G01N 33/38* (2006.01)
*G06T 3/4038* (2024.01)
*H04N 23/698* (2023.01)

(52) U.S. Cl.
CPC ........... *G01N 21/95* (2013.01); *G01N 33/383* (2013.01); *G06T 3/4038* (2013.01); *G06T 7/0002* (2013.01); *H04N 23/698* (2023.01); *G06T 2200/24* (2013.01); *G06T 2207/20081* (2013.01); *G06T 2207/30108* (2013.01); *G06T 2207/30132* (2013.01); *G06T 2207/30168* (2013.01); *G06T 2207/30184* (2013.01)

(58) Field of Classification Search
CPC . G06T 2207/30108; G06T 2207/30132; G06T 2207/30168; G06T 2207/30184; G01N 21/8851; G01N 21/892; G01N 21/95; G01N 33/383
See application file for complete search history.

(56) References Cited

U.S. PATENT DOCUMENTS

| | | | |
|---|---|---|---|
| 2011/0150326 A1 | 6/2011 | Jeong et al. | |
| 2017/0270650 A1* | 9/2017 | Howe | G06F 18/24133 |
| 2017/0343481 A1 | 11/2017 | Jahanshahi et al. | |
| 2018/0293725 A1 | 10/2018 | Ohshima | |
| 2019/0137409 A1 | 5/2019 | Nogami et al. | |
| 2023/0112828 A1* | 4/2023 | Horita | G06V 30/10 356/237.1 |

FOREIGN PATENT DOCUMENTS

| | | | | |
|---|---|---|---|---|
| JP | 2001-099784 A | | 4/2001 | |
| JP | 4006007 B2 | | 11/2007 | |
| JP | 2010-538258 A | | 12/2010 | |
| JP | 2013-228232 A | | 11/2013 | |
| JP | 2014202922 A | * | 10/2014 | ......... H04N 5/23212 |
| JP | 2017085432 A | * | 5/2017 | ............. H04N 5/232 |
| WO | 2016/189764 A1 | | 12/2016 | |
| WO | 2017/103982 A1 | | 6/2017 | |
| WO | 2017/221706 A1 | | 12/2017 | |
| WO | 2018/008370 A1 | | 1/2018 | |
| WO | WO-2019031086 A1 | * | 2/2019 | ............... G06T 1/00 |
| WO | WO-2020008973 A1 | * | 1/2020 | ......... H04N 5/23222 |

OTHER PUBLICATIONS

International Search Report issued in PCT/JP2018/048178; dated Apr. 2, 2019.
International Preliminary Report on Patentability and Written Opinion issued in PCT/JP2018/048178; dated Aug. 4, 2020.
Wenyu Zhang et al.; "Automatic Crack Detection and Classification Method for Subway Tunnel Safety Monitoring"; SENSORS, vol. 14, No. 10, Oct. 16, 2014; pp. 19307-19328; XP055528998; doi:10.3390/s141019307.
Gang Li et al.; "Long-distance precision inspection method for bridge cracks with image processing"; Automation in Construction; ELSEVIER; vol. 41; May 1, 2014; pp. 83-95; XP009524929; Amsterdam, Netherlands.
The extended European search report issued by the European Patent Office dated Jan. 26, 2021, which corresponds to European Patent Application No. 18903103.3-1210 and is related to U.S. Appl. No. 16/935,988.
Communication pursuant to Article 94(3) EPC issued by the European Patent Office on Oct. 7, 2022, which corresponds to European Patent Application No. 18903103.2-1210 and is related to U.S. Appl. No. 16/935,988.
An Office Action mailed by China National Intellectual Property Administration dated Feb. 3, 2023, which corresponds to Chinese Patent Application No. 201880088379.2 and is related to U.S. Appl. No. 16/935,988; with English language translation.
An Office Action mailed by China National Intellectual Property Administration dated Aug. 30, 2023, which corresponds to Chinese Patent Application No. 201880088379.2 and is related to U.S. Appl. No. 16/935,988; with English language translation.
An Office Action mailed by China National Intellectual Property Administration on Jan. 22, 2024, which corresponds to Chinese Patent Application No. 201880088379.2 and is related to U.S. Appl. No. 16/935,988; with English language translation.

* cited by examiner

FIG. 9A

| IMAGE ID | PARTIAL IMAGE ID | CHECK DETERMINATION | CRACK ID | START POINT (X,Y) | END POINT (X,Y) | LENGTH (mm) | THICKNESS (mm) | DETECTION METHOD | CHECKING |
|---|---|---|---|---|---|---|---|---|---|
| R001 | R001-1 | CHECK TARGET | R001-1-1 | (x1,y1) | (x11,y11) | 31 | 0.09 | AUTOMATIC DETECTION | COMPLETED |
| | | | R001-1-2 | (x2,y2) | (x12,y12) | 27 | 0.11 | AUTOMATIC DETECTION | COMPLETED |
| | R001-2 | | R001-2-1 | (x3,y3) | (x13,y13) | 35 | 0.11 | AUTOMATIC DETECTION | NOT COMPLETED |
| | | | R001-2-2 | (x4,y4) | (x14,y14) | 14 | 0.08 | AUTOMATIC DETECTION | NOT COMPLETED |
| | R001-3 | | R001-3-1 | (x5,y5) | (x15,y15) | 28 | 0.06 | AUTOMATIC DETECTION | NOT COMPLETED |
| R002 | R002-1 | CHECKING NOT NECESSARY | R002-1-1 | (x6,y6) | (x16,y16) | 29 | 0.10 | AUTOMATIC DETECTION | — |
| | R002-2 | CHECKING NOT NECESSARY | R002-2-1 | (x7,y7) | (x17,y17) | 34 | 0.05 | AUTOMATIC DETECTION | — |
| | | | R002-2-2 | (x8,y8) | (x18,y18) | 32 | 0.05 | AUTOMATIC DETECTION | — |
| ..... | ..... | ..... | ..... | ..... | ..... | ..... | ..... | ..... | ..... |

FIG. 9B

| IMAGE ID | PARTIAL IMAGE ID | CHECK DETERMINATION | CRACK ID | START POINT (X,Y) | END POINT (X,Y) | LENGTH (mm) | THICKNESS (mm) | DETECTION METHOD | CHECKING |
|---|---|---|---|---|---|---|---|---|---|
| R001 | R001-1 | CHECK TARGET | R001-1-1 | (x1,y1) | (x11,y11) | 31 | 0.09 | AUTOMATIC DETECTION | COMPLETED |
| | | | R001-1-2 | (x2,y2) | (x12,y12) | 27 | 0.11 | AUTOMATIC DETECTION | COMPLETED |
| | R001-2 | | R001-2-1 | (x3,y3) | (x13,y13) | 35 | 0.11 | AUTOMATIC DETECTION | COMPLETED |
| | | | R001-2-2 | (x4,y4) | (x14,y14) | 14 | 0.08 | AUTOMATIC DETECTION | COMPLETED |
| | R001-3 | | R001-3-1 | (x5,y5) | (x15,y15) | 28 | 0.06 | AUTOMATIC DETECTION | COMPLETED |
| | | | R001-3-2 | (x9,y9) | (x19,y19) | 33 | 0.10 | MANUAL ADDITION | COMPLETED |
| ..... | ..... | ..... | ..... | ..... | ..... | ..... | ..... | ..... | ..... |

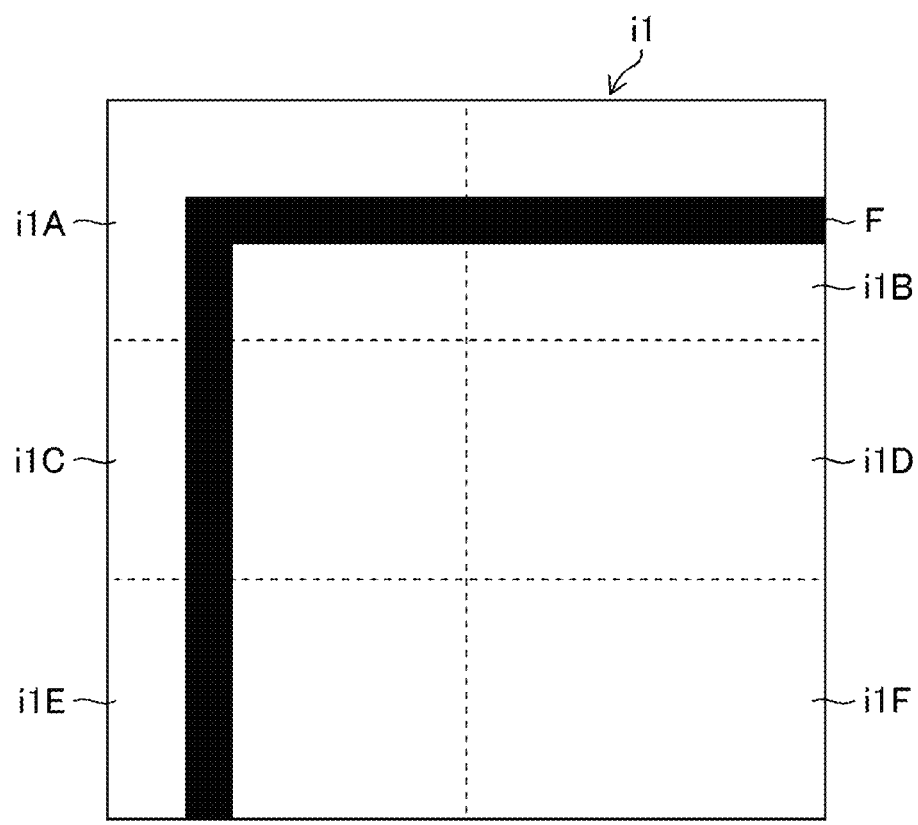

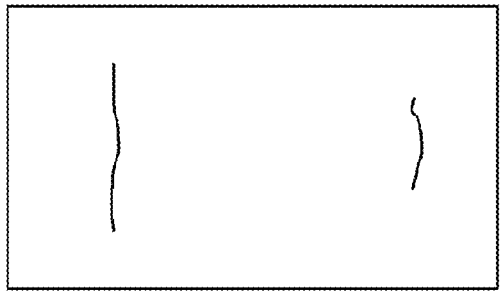
FIG. 27A
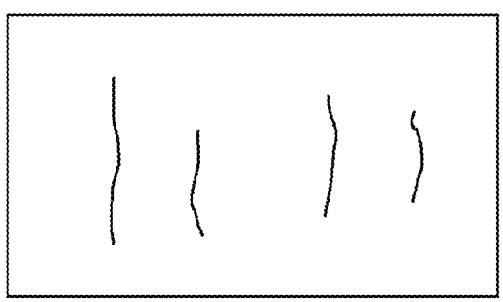
FIG. 27B
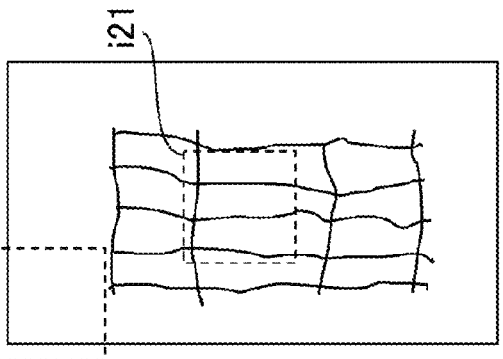
FIG. 27C
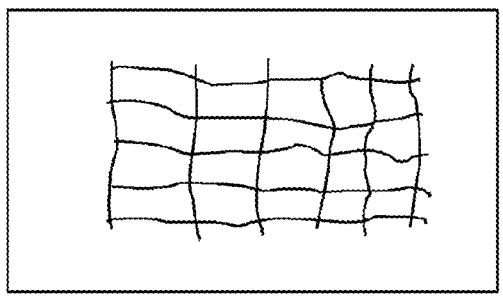
FIG. 27D
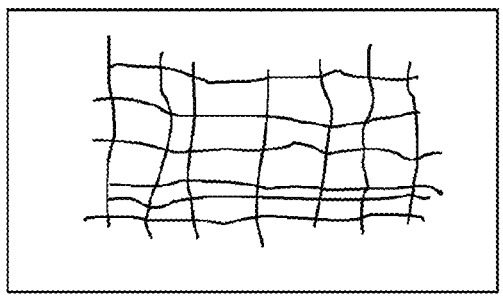
FIG. 27E
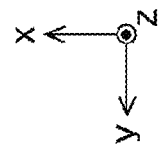

IMAGE PROCESSING APPARATUS AND IMAGE PROCESSING METHOD

CROSS-REFERENCE TO RELATED APPLICATIONS

The present application is a Continuation of PCT International Application No. PCT/JP2018/048178 filed on Dec. 27, 2018 claiming priority under 35 U.S.C § 119(a) to Japanese Patent Application No. 2018-017280 filed on Feb. 2, 2018. Each of the above applications is hereby expressly incorporated by reference, in its entirety, into the present application.

BACKGROUND OF THE INVENTION

1. Field of the Invention

The present invention relates to an image processing apparatus and an image processing method for detecting damage to a photographic subject from images acquired by photographing the photographic subject.

2. Description of the Related Art

In the field of image processing, a technique in which a photographic subject, such as a building or a structure, is photographed and damage (cracks, corrosion, peeling, etc.) to the photographic subject is detected from the acquired images is known. In detection of damage, depending on the photographic subject (for example, a bridge, a road, a building, etc.), a composite image that represents a wide area (the entire inspection area or part thereof) is created on the basis of a large number of images acquired by photographing. For example, JP2001-99784A describes a technique in which cracks are detected from images acquired by photographing a bridge to create an extensive distribution map of the cracks.

SUMMARY OF THE INVENTION

In a case of detecting damage from images, there is a case where omission in detection and/or erroneous detection may be possibly present due to the characteristics of the photographic subject, the photographing conditions, etc., and a user may check and revise such detection results. For such checking and revision, a large number of images may be captured depending on conditions including the size of the photographic subject, the inspection area, etc. In a case of checking and revising all the images, even an image having a reduced need for checking and revision (for example, an image for which damage is correctly detected) becomes a target, which leads to work that takes a lot of time.

In a case where a composite image that represents a wide area is a target in checking and revision, the following problems may occur. For example, in a case where the composite image is displayed in the actual size and, for example, enlarged and scrolled to check the image, the user may lose track of the area that the user has checked, which may result in omission in checking, duplicated checking (the same region is checked a plurality of times), etc. Depending on the size of the photographic subject, the image size of the composite image (the memory usage in the image processing apparatus) increases, and problems may occur in which, for example, screen display becomes slow or display fails. On the other hand, in a case where the composite image is reduced and checked, the resolution decreases, and it may be difficult to check damage. Depending on image processing that is performed at the time of composition (overlapping in a region in which a plurality of images overlap, a tilt correction, etc.), there is the possibility that checking of damage that can be checked on an image before composition fails on the composite image.

However, JP2001-99784A mentioned above only describes a technique for outputting and displaying each small section and reducing or enlarging each small section and does not take into consideration reduction in the time taken for checking and revision.

Accordingly, with the related art, it is not possible to efficiently check or revise the results of damage detection.

The present invention has been made in view of the above-described circumstances, and an object thereof is to provide an image processing apparatus and an image processing method with which a user can efficiently check and revise the results of damage detection.

To achieve the above-described object, an image processing apparatus according to a first aspect of the present invention includes: an image receiving unit that receives a plurality of images acquired by photographing a photographic subject in sections; a damage detection unit that detects damage to the photographic subject from individual images that are images individually forming the plurality of images; an image determination unit that determines whether each individual image among the individual images is to be regarded as a check target image for which a user is encouraged to check a detection result for the individual image; a display control unit that displays on a display device the check target image or a partial image cut from a partial region of the check target image so as to fit in a display region of the display device in association with the detection result for the check target image or for the partial image; and a detection result revising unit that revises the detection result on the basis of an instruction input by the user.

In the first aspect, among the individual images, a detection result for the check target image for which it is determined that "a user is encouraged to check the detection result" or a detection result for the partial image acquired by cutting a partial region from the check target image is displayed on the display device to encourage the user to check the detection result, and the detection result is revised on the basis of an instruction input by the user. Therefore, the image for which the detection result is to be checked is distinctively displayed, and the detection result for the image is revised on the basis of an instruction input by the user, which results in reduction in the time taken for checking and revision. As the "revision" of the detection result, the image processing apparatus can make, for example, addition (adding information about damage omitted in detection), correction (correcting an incorrect detection result to a correct result), and deletion (deleting information about erroneously detected damage). The image processing apparatus performs the above-described "revision" on the basis of an instruction input by the user.

The image processing apparatus (display control unit) can cut the partial image from the check target image in accordance with the resolution of the display region. For example, in a case where the number of pixels (resolution) of the check target image is equal to or smaller than the number of pixels (resolution) of the display region, the display control unit can display the check target image, and in a case where the number of pixels of the check target image exceeds the number of pixels of the display region, the display control unit can cut a part from the check target image as the partial image. Accordingly, the number of pixels (resolution) of the displayed image does not decrease, and a situation where it is difficult or it is not possible to check damage due to the reduced image does not occur. Accordingly, the user can precisely check and revise the detection result.

Note that in the first aspect, the state where the display control unit "displays" the image (check target image or partial image) "in association with" the detection result includes a state where the display control unit superimposes and displays the image and information (a character, a numeral, a figure, a symbol, etc.) indicating the detection result for the image. The display control unit may display the information indicating the detection result in a color and/or with brightness that differs depending on the degree of the damage. The display of the information indicating the detection result may be turned on and off in accordance with a user instruction.

Accordingly, with the first aspect, the user can efficiently check and revise the result of damage detection.

An image processing apparatus according to a second aspect is the image processing apparatus according to the first aspect in which the display control unit displays on the display device a non-check target image among the plurality of images and a detection result for the non-check target image so as to be distinguishable from the check target image and the detection result for the check target image. In the second aspect, the display control unit displays the check target image and the non-check target image, and the detection results in the respective images in a distinguishable manner, and therefore, the user can easily grasp the check target region and its detection result and can efficiently check and revise the detection result. Note that in the second aspect and the subsequent aspects, an image that is not the check target image among the plurality of images acquired by photographing the photographic subject can be regarded as "non-check target image".

An image processing apparatus according to a third aspect is the image processing apparatus according to the first or second aspect in which in response to an input instruction indicating that the user has checked and/or revised a detection result in one check target image, the display control unit displays another check target image and a detection result for the other check target image. In the third aspect, in response to an input instruction indicating checking and/or revision of a detection result for one check target image, the display control unit displays a result for another image, and therefore, the possibility of omission in checking can be reduced.

An image processing apparatus according to a fourth aspect is the image processing apparatus according to any one of the first to third aspects in which after detection results have been checked and/or revised for all regions of one check target image, the display control unit displays another check target image and a detection result for the other check target image. In the fourth aspect, after detection results have been checked and/or revised for all regions of one check target image, the display control unit displays another check target image and a detection result for the other check target image. Therefore, the possibility of omission in checking can be reduced.

An image processing apparatus according to a fifth aspect is the image processing apparatus according to any one of the first to fourth aspects in which the image determination unit performs determination on the basis of at least one of image quality of the individual image, the detection result, a photographing condition, or a construction of the photographic subject. In the fifth aspect, specific criteria for determining whether to regard each individual image as the check target image are indicated.

An image processing apparatus according to a sixth aspect is the image processing apparatus according to the fifth aspect in which the image determination unit obtains the image quality on the basis of at least one of a result of evaluation by an image quality evaluator configured by machine learning, a spatial frequency spectrum of the individual image, or a density histogram of the individual image. In the sixth aspect, specific criteria for determining the image quality are indicated.

An image processing apparatus according to a seventh aspect is the image processing apparatus according to any one of the first to sixth aspects in which the image determination unit performs determination on the basis of the number and/or density of detection results, in the individual image, for each of which a degree of certainty indicating actual damage is equal to or larger than a threshold. In the seventh aspect, the image determination unit can determine, for example, an image for which the number of detection results for each of which the degree of certainty is equal to or larger than a threshold is small and/or an image for which the density of detection results for each of which the degree of certainty is equal to or larger than the threshold is low to be the check target image. In such an image, omission in detection, erroneous detection, etc. is highly likely to occur. When the image is determined to be the check target image, the user can efficiently check and revise the detection result.

An image processing apparatus according to an eighth aspect is the image processing apparatus according to the seventh aspect in which the display control unit displays each detection result in a distinguishable manner in accordance with the degree of certainty. With the eighth aspect, the user can easily grasp the degree of certainty of each detection result with distinguishable display and can take an action, such as selective and intensive checking of a detection result for which the degree of certainty is low. Accordingly, the user can efficiently check and revise the detection result. Note that in the eighth aspect, each detection result can be displayed in a distinguishable manner by, for example, the display control unit changing a character, a numeral, a figure, a symbol, a color, brightness, etc. indicating the detection result in accordance with the degree of certainty.

An image processing apparatus according to a ninth aspect is the image processing apparatus according to the seventh or eighth aspect in which the display control unit displays in a distinguishable manner a region, in the check target image or in the partial image, in which a detection result for which the degree of certainty is equal to or larger than the threshold is present. With the ninth aspect, the user can easily distinguish a region in which the degree of certainty of a detection result is high (equal to or larger than the threshold) and a region in which the degree of certainty is low (smaller than the threshold) from each other with distinguishable display, and can take an action, such as selective or intensive checking and revision of a detection result for which the degree of certainty is low.

An image processing apparatus according to a tenth aspect is the image processing apparatus according to any one of the first to ninth aspects in which the image determination unit includes a depth-of-field calculation unit that calculates a depth of field of each individual image, and in a case where the individual image includes a region outside a range of the depth of field, the image determination unit determines that the individual image is to be regarded as the check target image. In the region outside the range of the depth of field (for example, the in-focus degree is smaller than a threshold), omission in detection, erroneous detection, etc. is highly likely to occur due to blurring in the image, and the image is in great need for checking and/or revision accordingly. From this viewpoint, in the tenth aspect, the image determination unit determines an individual image that includes a region outside the range of the depth of field to be the check target image. Accordingly, the user can efficiently check and revise the detection result.

An image processing apparatus according to an eleventh aspect is the image processing apparatus according to the tenth aspect in which the depth-of-field calculation unit calculates the depth of field on the basis of a photographing angle of the photographic subject in the check target image and an in-focus position in the check target image. A region away from the in-focus position in an angle change direction relative to the photographic subject is outside the depth of field and is blurred. Therefore, it is preferable to calculate the depth of field as in the eleventh aspect.

An image processing apparatus according to a twelfth aspect is the image processing apparatus according to the tenth or eleventh aspect in which the depth-of-field calculation unit calculates the depth of field on the basis of a photographing angle of the photographic subject, a photographing distance to the photographic subject, an aperture value used when the check target image is captured, and a permissible circle of confusion diameter.

An image processing apparatus according to a thirteenth aspect is the image processing apparatus according to any one of the tenth to twelfth aspects in which the display control unit displays in a distinguishable manner a region, in the check target image or in the partial image, outside the range of the depth of field. With the thirteenth aspect, the user can easily distinguish a region within the range of the depth of field (a region for which damage is highly likely to be correctly detected) and a region outside the range (a region that is blurred and for which erroneous detection or omission in detection is highly likely to occur) from each other with distinguishable display, and can efficiently check and revise the detection result. Note that distinguishable display can be performed by the display control unit adding different characters, numerals, figures, symbols, colors, etc. to the region within the range of the depth of field and to the region outside the range or changing the degrees thereof.

An image processing apparatus according to a fourteenth aspect is the image processing apparatus according to any one of the tenth to thirteenth aspects in which the display control unit displays in a distinguishable manner a check target region, in the check target image, set in accordance with curvature of field of an imaging optical system and an in-focus position. In a case where curvature of field occurs due to the characteristics of the imaging optical system (imaging lens), when the center part of an image is in focus, the peripheral part is blurred, and when the peripheral part is in focus, the center part is blurred. When the display control unit performs distinguishable display as in the fourteenth aspect, the user can easily distinguish a region in which the in-focus degree is high and a region in which the in-focus degree is low from each other, and can efficiently check and revise the detection result. An area that is an in-focus region differs depending on the characteristics of the imaging optical system, and therefore, it is preferable to create in advance a database and to acquire and use data of the imaging optical system that is used in actual photographing.

An image processing apparatus according to a fifteenth aspect is the image processing apparatus according to any one of the first to fourteenth aspects in which in a case where the individual image is captured while strobe light is flashed and where the individual image includes a low-luminance region that is set in accordance with a change in luminance caused by an arrangement of a light source of the strobe light and an imaging optical system, the image determination unit determines that the individual image is to be regarded as the check target image. In an image, a region away from the flashing direction of the strobe light (for example, the peripheral part of the image) becomes dark (the luminance decreases), and omission in detection, erroneous detection, etc. is highly likely to occur. From this viewpoint, in the fifteenth aspect, the image determination unit determines an individual image that includes a low-luminance region to be the check target image, and the user can efficiently correct and revise the detection result accordingly.

An image processing apparatus according to a sixteenth aspect is the image processing apparatus according to the fifteenth aspect in which the low-luminance region is a region set on the basis of a photographing distance. As the photographing distance is shorter, the dark region (low-luminance region) becomes wider, and as the photographing distance is longer, the dark region becomes narrower. When the photographing distance is further longer, the luminance becomes almost uniform, and the dark region is lost. In the sixteenth aspect, it is preferable to create in advance a database indicating such a relationship between the photographing distance and the dark region.

An image processing apparatus according to a seventeenth aspect is the image processing apparatus according to the fifteenth or sixteenth aspect in which the display control unit displays in a distinguishable manner the low-luminance region in the check target image or in the partial image. In the low-luminance region, omission in detection, erroneous detection, etc. is highly likely to occur, and the region is in great need for checking and revision. In the seventeenth aspect, the display control unit displays the low-luminance region in a distinguishable manner, and the user can efficiently check and revise the detection result accordingly.

An image processing apparatus according to an eighteenth aspect is the image processing apparatus according to any one of the first to seventeenth aspects further including a construction information acquisition unit that acquires construction information indicating a construction of the photographic subject, in which in a case of determining with reference to the construction information that a photographing area of the individual image includes a region in which damage is likely to occur, the image determination unit determines that the individual image is to be regarded as the check target image. The region in which damage is likely to occur is a region that is in great need for correction and revision. In the eighteenth aspect, the image determination unit determines an individual image that includes a region in which damage is likely to occur to be the check target image. Examples of the "region in which damage is likely to occur" include a region on which a heavy load is put, a joint part of members, an intermediate part, and a location where the shape of a member changes, but are not limited to these.

An image processing apparatus according to a nineteenth aspect is the image processing apparatus according to any one of the first to eighteenth aspects further including: a parameter calculation unit that calculates a parameter for performing panoramic composition of the plurality of images; and an overlap calculation unit that calculates an overlap region between the plurality of individual images on the basis of the parameter, in which in a case where the overlap region has been checked in any image or in a case where the overlap region is other than a region having highest image quality, the display control unit displays the overlap region in a distinguishable manner. In the case where the overlap region has been checked, the overlap region has a reduced need for re-checking. On the other hand, in the case where the overlap region is other than a region having highest image quality, the reliability of the detection result is (relatively) low, and it is preferable to check and revise the detection result for the "region having highest image quality". With the nineteenth aspect, the user can refer to distinguishable display and efficiently check and revise the detection result for the overlap region.

An image processing apparatus according to a twentieth aspect is the image processing apparatus according to the nineteenth aspect further including an image composition unit that generates a panoramic composite image from the plurality of images on the basis of the parameter, in which the display control unit displays in a distinguishable manner an area, in the panoramic composite image, represented by the check target image. With the twentieth aspect, the user can easily grasp an area, in the entire image (panoramic composite image), occupied by the check target image.

An image processing apparatus according to a twenty-first aspect is the image processing apparatus according to the twentieth aspect in which the display control unit displays in a distinguishable manner an area that has been checked and/or revised in the panoramic composite image. In the twenty-first aspect, the area that has been checked and/or revised is displayed in a distinguishable manner, which can reduce the possibility of omission, duplication, etc. in checking and/or revision.

An image processing apparatus according to a twenty-second aspect is the image processing apparatus according to the twentieth or twenty-first aspect in which the image composition unit calculates information indicating a correspondence between the panoramic composite image and the plurality of images, and the display control unit displays on the display device an image, among the plurality of images, corresponding to an area specified in the panoramic composite image on the basis of the information. In the twenty-second aspect, the display control unit displays the image (and the detection result) corresponding to the area specified in the panoramic image on the basis of the information indicating the correspondence. Therefore, the user can specify a desired area and efficiently check and revise the detection result.

An image processing apparatus according to a twenty-third aspect is the image processing apparatus according to any one of the first to twenty-second aspects further including an image capturing unit that captures an image of the photographic subject with an imaging optical system and an imaging element on which an optical image of the photographic subject is formed by the imaging optical system, in which the image receiving unit receives, as the plurality of images, a plurality of images captured by the image capturing unit. In the twenty-third aspect, the images captured by the image capturing unit can be received by the image receiving unit to, for example, detect damage.

To achieve the above-described object, an image processing method according to a twenty-fourth aspect of the present invention includes: an image receiving step of receiving a plurality of images acquired by photographing a photographic subject in sections; a damage detection step of detecting damage to the photographic subject from individual images that are images individually forming the plurality of images; an image determination step of determining whether each individual image among the individual images is to be regarded as a check target image for which a user is encouraged to check a detection result for the individual image; a display control step of displaying on a display device the check target image or a partial image cut from a partial region of the check target image so as to fit in a display region of the display device in association with the detection result for the check target image or for the partial image; and a detection result revising step of revising the detection result on the basis of an instruction input by the user. With the twenty-fourth aspect, the user can efficiently check and revise the result of damage detection as in the first aspect. Note that in the twenty-fourth aspect, the configurations the same as in the second to twenty-third aspects may be further included. Further, aspects of the present invention also include a program that causes a computer or an image processing apparatus to perform the image processing method according to these aspects and a non-transitory recording medium to which a computer-readable code of the program is recorded.

As described above, with the image processing apparatus and the image processing method according to the present invention, a user can efficiently check and revise the results of damage detection.

BRIEF DESCRIPTION OF THE DRAWINGS

FIGS. 9A and 9B are tables illustrating the results of damage detection before and after revision;

FIG. 10 is a diagram illustrating a state where partial images are cut;

FIGS. 27A to 27E are diagrams illustrating a state where cracks appear in a floor slab;

DESCRIPTION OF THE PREFERRED EMBODIMENTS

Hereinafter, embodiments of an image processing apparatus and an image processing method according to the present invention will be described in detail with reference to the attached drawings.

Construction of Bridge

Figure 1:
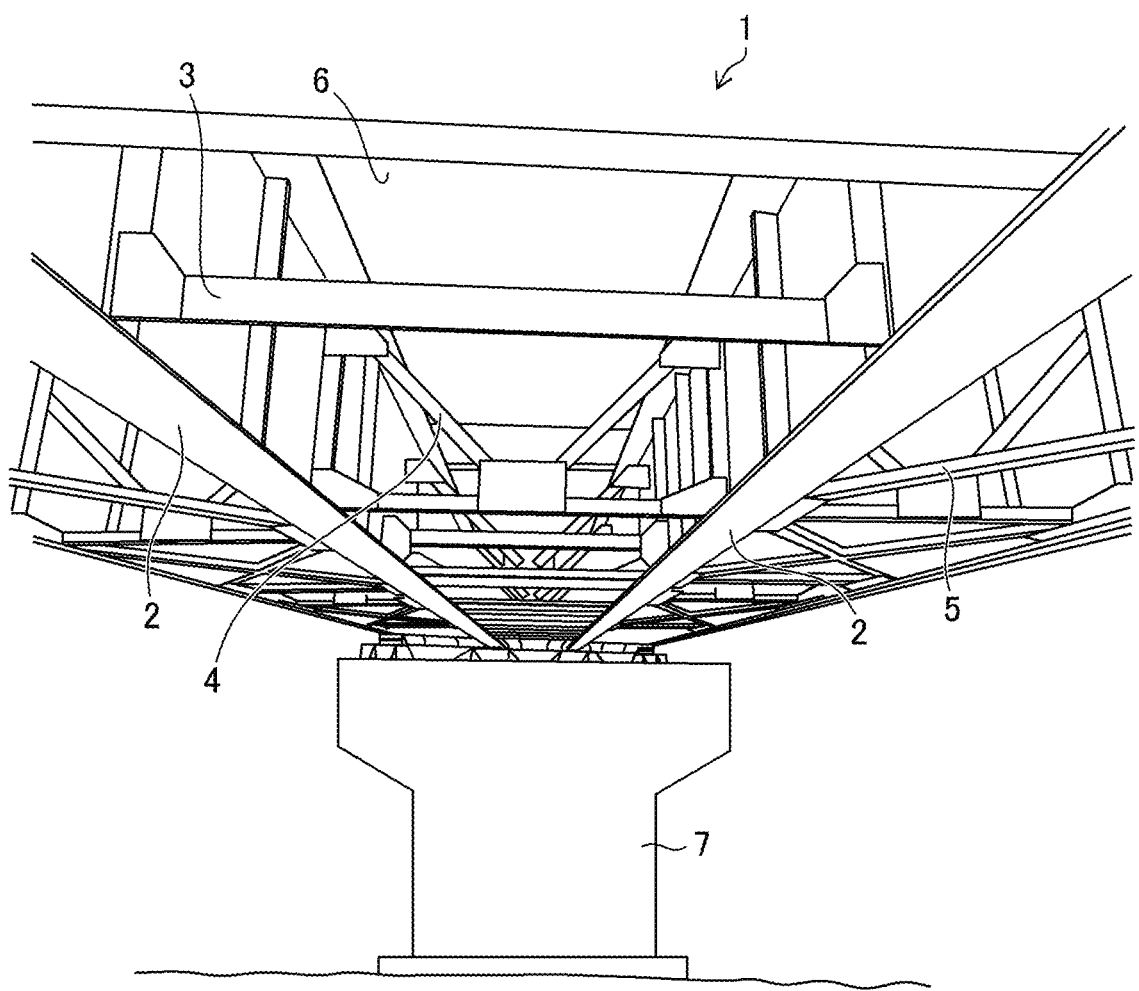
FIG. 1 is an external view of a bridge when viewed from the underside.

FIG. 1 is a perspective view of a bridge 1, which is a structure, when viewed from underneath. The bridge 1 illustrated in FIG. 1 has a three-dimensional construction constituted by main girders 2, cross girders 3, sway bracing 4, lateral bracing 5, a floor slab 6, and piers 7 and is constructed by coupling these members with bolts, rivets, etc. and by welding, etc. Over the main girders 2, etc., the floor slab 6 on which vehicles, etc. are traveling is formed by pouring concrete. The floor slab 6 is typically built of reinforced concrete. The main girders 2 are members that are laid between the piers 7 to bear the load of vehicles, etc. traveling on the floor slab 6, and have a plane (plane in the vertical direction) orthogonal to a plane (horizontal plane) of the floor slab 6. The cross girders 3 are members that each couple the main girders 2 so that the plurality of main girders 2 bear the load. The sway bracing 4 and the lateral bracing 5 are members that couple the main girders 2 with each other to resist lateral loads imposed by winds and earthquakes. Note that in this embodiment, a case where the bridge 1 is a target (photographic subject) is described; however, the target structure is not limited to a bridge and may be a tunnel, a building, a road, etc.

Acquisition of Images

In a case of capturing images of the bridge 1 to detect damage, an inspector uses a digital camera 100 (see FIG. 2) to photograph the bridge 1 and acquires a plurality of captured images of an inspection area in sections (a plurality of images respectively acquired by photographing different parts of the bridge 1). The inspector photographs the bridge 1 while moving in the extending direction of the bridge 1 and the direction orthogonal to the extending direction as appropriate. Note that in a case where the inspector has difficulty in moving due to the circumstances of the bridge 1, the digital camera 100 may be mounted in a mobile object that is movable along the bridge 1 to carry out photographing. Such a mobile object may be provided with a mechanism for raising and lowering the digital camera 100 or a mechanism for rotating the digital camera 100 (a mechanism for panning and/or tilting). Examples of the mobile object include a vehicle, a robot, and an aircraft (drone, etc.) but are not limited to these.

First Embodiment

Configuration of Image Processing Apparatus

Figure 2:
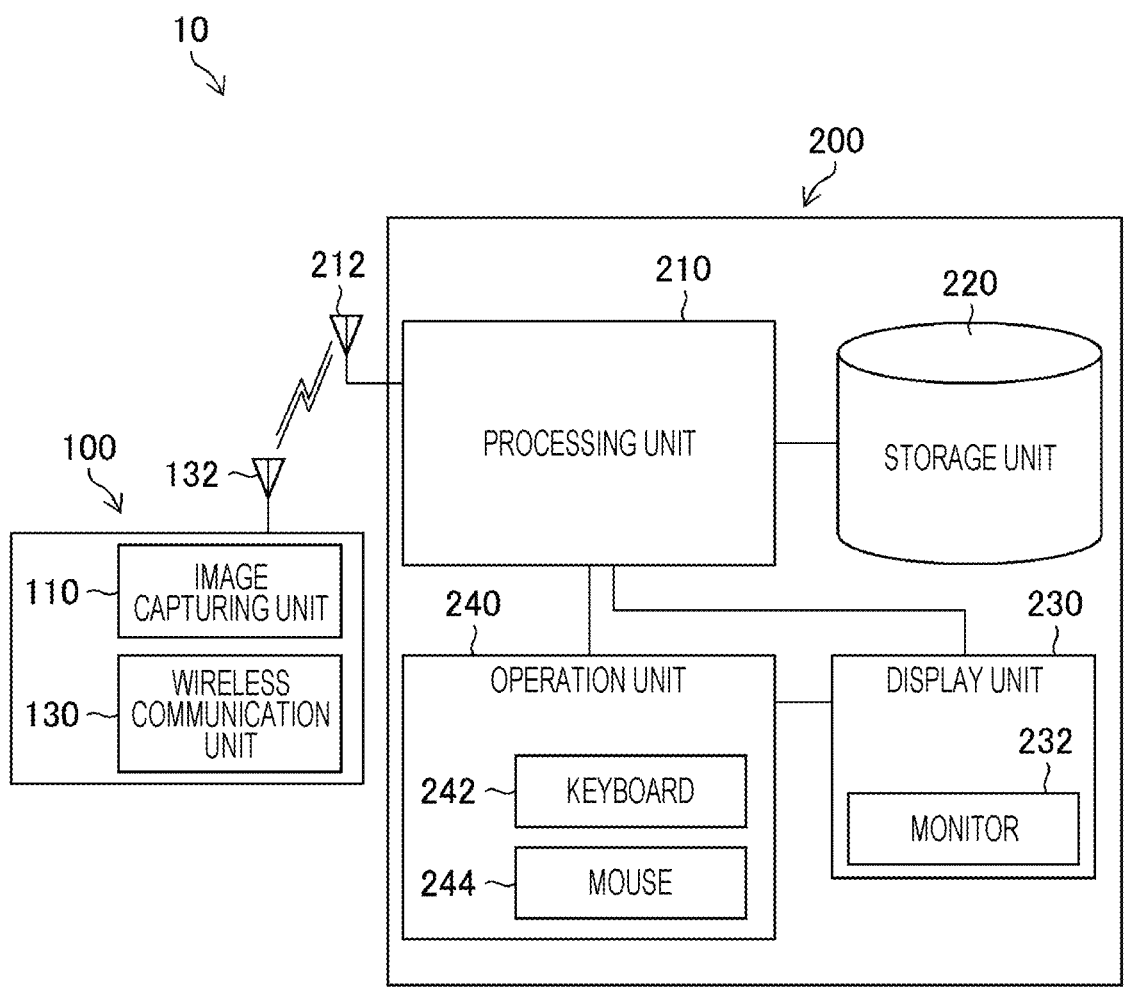
FIG. 2 is a block diagram illustrating a configuration of an image processing apparatus according to a first embodiment.

FIG. 2 is a block diagram schematically illustrating a configuration of an image processing apparatus 10 (image processing apparatus). The image processing apparatus 10 includes the digital camera 100 and an image processing apparatus main body 200 and is a system for, for example, detecting damage from a plurality of images acquired by photographing a photographic subject in sections and for composing detection results. In the image processing apparatus 10, a personal computer, a tablet terminal, a smartphone, or any other device (information terminal) can be used as the image processing apparatus main body 200. The components of the image processing apparatus 10 may be accommodated in one housing or may be accommodated in separate housings. The components may be placed at different places and connected to one another via a network.

Configuration of Digital Camera

The digital camera 100 acquires images with an image capturing unit 110 that includes an imaging lens (imaging optical system) not illustrated and an imaging element (imaging element) not illustrated on which an optical image of a photographic subject is formed by the imaging lens. Examples of the imaging element include a CCD (charge-coupled device) imaging element and a CMOS (complementary metal-oxide semiconductor) imaging element. On the photosensitive surface of the imaging element, R (red), G (green), and B (blue) color filters are provided, and a color image of a photographic subject can be acquired on the basis of signals of the respective colors. The digital camera 100 wirelessly communicates with the image processing apparatus main body 200 via a wireless communication unit 130 and an antenna 132, captured images are input to a processing unit 210, and a process described below is performed. Note that the digital camera 100 may be built in a housing separate from the image processing apparatus main body 200 or may be integrated in the image processing apparatus main body 200.

Overall Configuration of Image Processing Apparatus Main Body

The image processing apparatus main body 200 includes the processing unit 210, a storage unit 220, a display unit 230, and an operation unit 240, and these units are connected to one another to transmit and receive necessary information. The image processing apparatus main body 200 wirelessly communicates with the digital camera 100 via an antenna 212 to acquire captured images captured by the digital camera 100.

Configuration of Processing Unit

Figure 3:
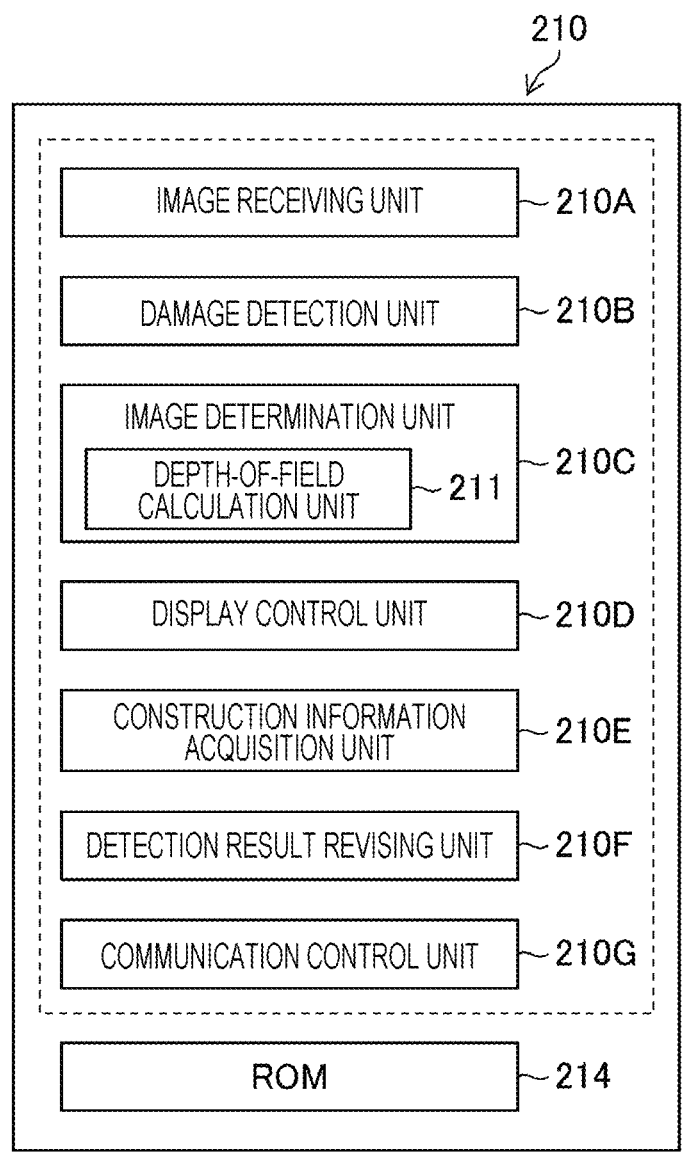
FIG. 3 is a diagram illustrating a configuration of a processing unit.

FIG. 3 is a diagram illustrating a configuration of the processing unit 210. The processing unit 210 includes an image receiving unit 210A, a damage detection unit 210B, an image determination unit 210C, a display control unit 210D, a construction information acquisition unit 210E, a detection result revising unit 210F, and a communication control unit 210G to, for example, receive captured images acquired by the digital camera 100, detect damage and make revision, and control display of a processing result on a monitor 232.

The image receiving unit 210A (image receiving unit) receives from the digital camera 100 (or a recording medium, a network, etc.) captured images (a plurality of images acquired by photographing the bridge 1 in sections). The damage detection unit 210B (damage detection unit) detects damage to the bridge 1 (photographic subject) from individual images that are images individually forming the captured images. The image determination unit 210C (image determination unit) determines whether each individual image is to be regarded as a check target image for which the user is encouraged to check detection results for the individual image. The image determination unit 210C includes a depth-of-field calculation unit 211 (depth-of-field calculation unit) that calculates the depth of field of each individual image. The display control unit 210D (display control unit) controls display of the acquired images, the results of damage detection, etc. on the monitor 232. The display control includes display of an image (a check target image or a partial image acquired by cutting a partial region from a check target image so as to fit in a display region of a display device) and detection results in the image on the monitor 232 (display device) in association with each other. At the time of display, an image and/or detection results are displayed in a distinguishable manner as necessary (which will be described below). The construction information acquisition unit 210E acquires construction information that indicates the construction of the photographic subject. The construction information may be acquired via a recording medium or may be acquired from a server, a database, etc. on a network via the communication control unit 210G. The detection result revising unit 210F (detection result revising unit) revises the results of damage detection on the basis of an instruction input by the user. The communication control unit 210G transmits and receives images and information to and from the digital camera 100 via the antenna 212. The communication control unit 210G transmits and receives data (images, processing results, etc.) to and from an external server, a database, etc. via a network not illustrated.

Some or all of the functions of the processing unit 210 may be implemented as a server on a network, and the image processing apparatus main body 200 may be responsible for, for example, receiving data, controlling communication, and displaying results. In this case, an application service provider-type system including the server on the network is configured.

The above-described functions of the processing unit 210 can be implemented by using various processors. The various processors include, for example, a CPU (central processing unit) that is a general-purpose processor implementing various functions by executing software (program). The above-described various processors include a GPU (graphics processing unit) that is specialized in image processing and a programmable logic device (PLD), such as an FPGA (field-programmable gate array), in which the circuit configuration is changeable after manufacture. Further, the above-described various processors include a dedicated electric circuit, such as an ASIC (application-specific integrated circuit), that is a processor having a circuit configuration designed exclusively for performing specific processing.

The functions of the respective units may be implemented as one processor or may be implemented as a plurality of processors of the same type or different types (for example, a plurality of FPGAs, or a combination of a CPU and an FPGA or a combination of a CPU and a GPU). A plurality of functions may be implemented as one processor. As the first example of configuring a plurality of functions as one processor, a form is possible where one or more CPUs and software are combined to form one processor, a representative example of which is a computer such as the image processing apparatus main body or the server, and where this processor implements the plurality of functions. As the second example thereof, a form is possible where a processor in which the functions of the entire system are implemented as one IC (integrated circuit) chip, a representative example of which is a system on chip (SoC), is used. As described above, the various functions are configured as a hardware configuration by using one or more of the above-described various processors. The hardware configuration of the processors is more specifically an electric circuit (circuitry) in which circuit elements such as semiconductor elements are combined.

For the above-described processors or electric circuit to execute software (program), a processor (computer)-readable code of the software to be executed is stored in advance in a non-transitory recording medium, such as a ROM (read-only memory), and the processors refer to the software. The software stored in advance in the non-transitory recording medium includes a program for receiving images and measuring a photographic subject. The code may be recorded to a non-transitory memory, such as various magneto-optical recording devices or a semiconductor memory, instead of the ROM. At the time of processing using the software, for example, a RAM (random access memory) is used as a temporary storage area, and data stored in, for example, an EEPROM (electronically erasable and programmable read-only memory) not illustrated can be referred to.

The processing unit 210 includes a ROM 214 (read-only memory, which is a non-transitory recording medium) in addition to the above-described units. To the ROM 214, a computer-readable code of a program (including a program for performing the image processing method according to the present invention) necessary for processing including acquisition of images, detection of damage, and transmission and reception of data is recorded.

Configuration of Storage Unit

Figure 4:
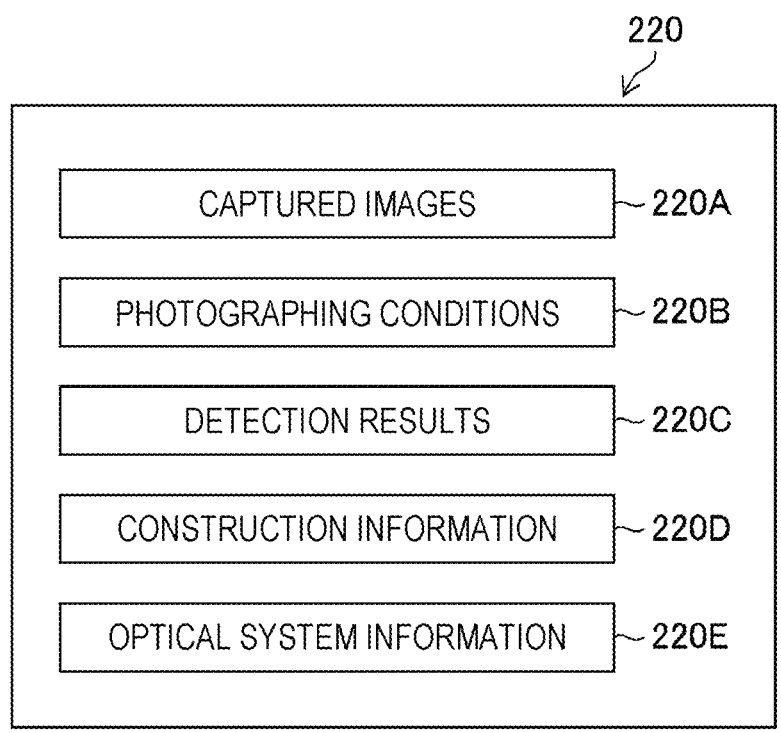
FIG. 4 is a diagram illustrating information stored in a storage unit.

The storage unit 220 is constituted by a non-transitory recording medium, such as a CD (compact disk), a DVD (digital versatile disk), a hard disk, semiconductor memories of various types, etc., and a control unit for the non-transitory recording medium, and stores images and information illustrated in FIG. 4 in association with each other. Captured images 220A are a plurality of images acquired by photographing in sections the bridge 1 (a part, such as the floor slab 6, the pier 7, the main girder 2, etc.), which is a photographic subject, with the digital camera 100 and received by the image receiving unit 210A. The storage unit 220 may store images acquired via a network or a recording medium instead of the images captured by the digital camera 100. Photographing conditions 220B are photographing conditions (date and time, place, exposure, etc.) for the captured images 220A. The photographing conditions 220B may be recorded as part of the captured images 220A (for example, in a header part) or may be recorded to a separate file and associated with the captured images 220A. Detection results 220C include the results of damage detection (see FIGS. 9A and 9B) for individual images that form the captured images 220A. The detection results 220C can be revised on the basis of an instruction input by the user (which will be described below). Construction information 220D is information indicating the construction of the photographic subject acquired by the construction information acquisition unit 210E. Optical system information 220E includes information (angle of view, focal length, aperture, various aberrations, etc.) indicating the characteristics of the imaging optical system.

Configurations of Display Unit and Operation Unit

The display unit 230 includes the monitor 232 (display device) and is capable of displaying received images, processing results, data stored in the storage unit 220, etc. The operation unit 240 includes a keyboard 242 and a mouse 244 each serving as an input device and/or a pointing device. The user can perform operations of, for example, giving an instruction for capturing images, an instruction for detecting damage, and an instruction for revising detection results necessary for performing the image processing method according to the present invention by using these devices and via the screen of the monitor 232 (which will be described below).

Procedure for Image Processing

Figure 5:
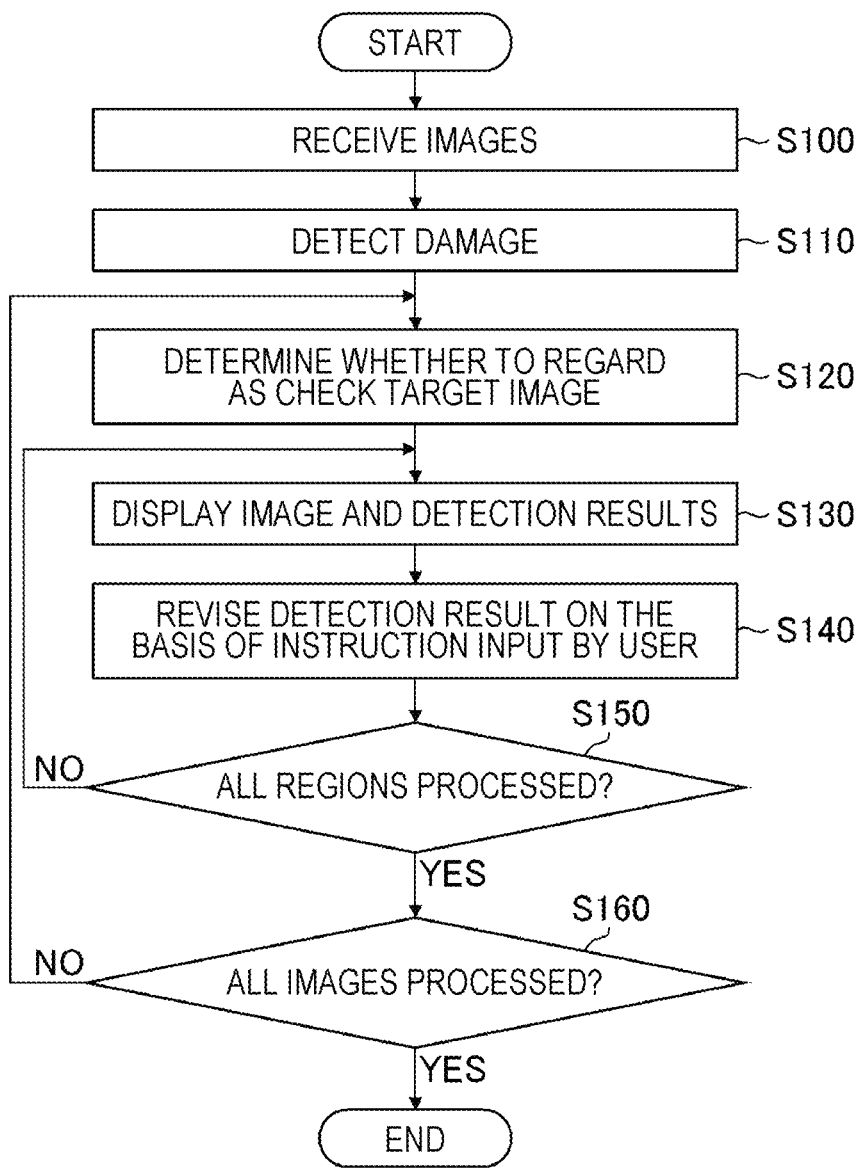
FIG. 5 is a flowchart illustrating a process in an image processing method according to the first embodiment.

Image processing that is performed by the image processing apparatus 10 is described. FIG. 5 is a flowchart illustrating a procedure for the image processing.

Reception of Images

Figure 6:
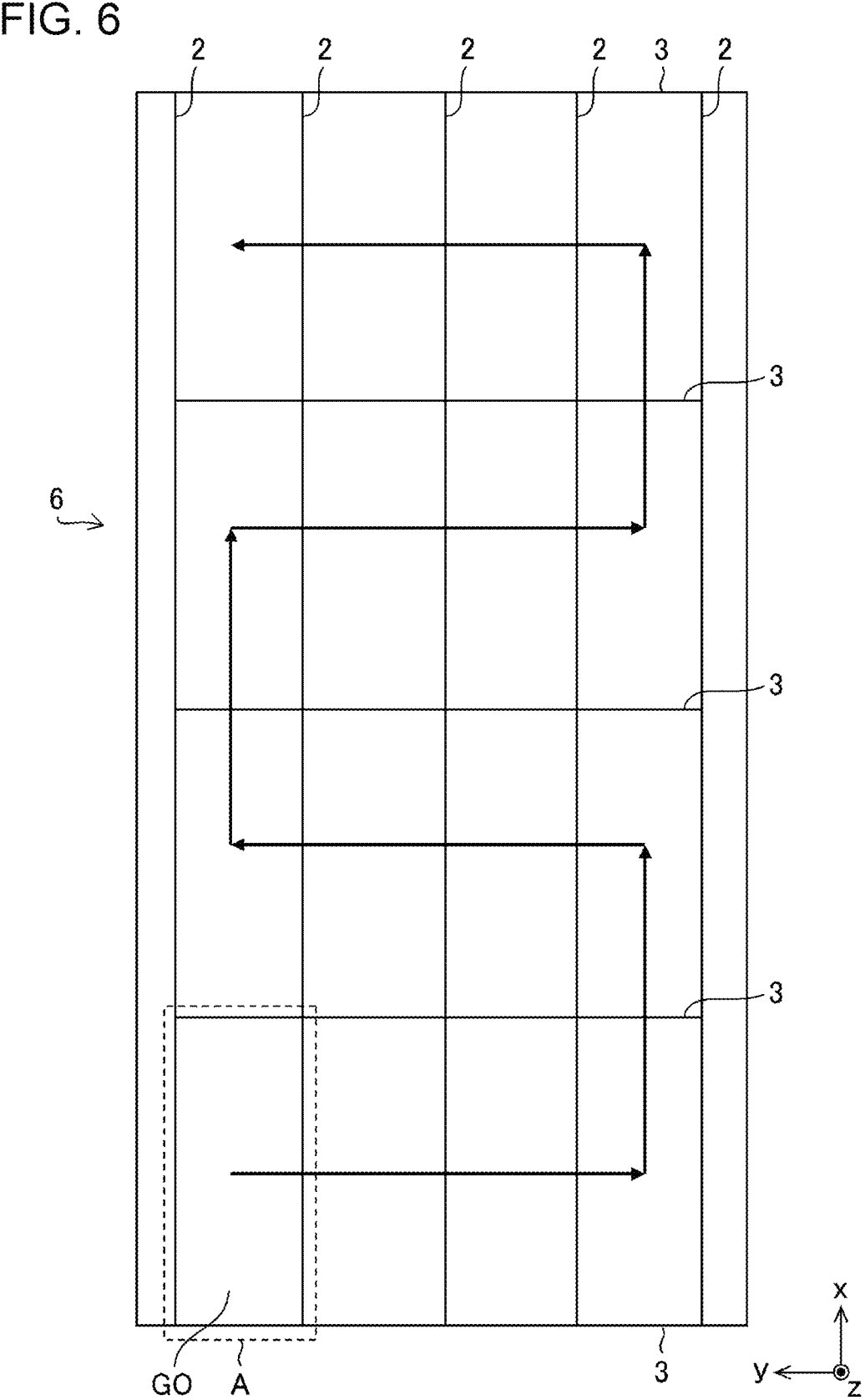
FIG. 6 is a diagram illustrating an example procedure for photographing a floor slab.

The image receiving unit 210A receives a plurality of images acquired by photographing the bridge 1 (photographic subject) in sections (step S100: image receiving step). A case where images of the floor slab 6 are captured by the digital camera 100 and received is described below; however, the photographic target is not limited to the floor slab 6 and may be the other part (for example, the main girder 2, the cross girder 3, the pier 7, etc.). Alternatively, images captured by other than the digital camera 100 may be received via a network, a recording medium, etc. FIG. 6 is a diagram illustrating an example procedure for photographing the floor slab 6. FIG. 6 illustrates a state where photographing is carried out in units of regions A each including a panel GO defined by corresponding ones of the main girders 2 (members extending in an x direction) and corresponding ones of the cross girders 3 (members extending in a y direction), and photographing is repeated while the photographic region is successively moved in the y direction and the x direction (in the directions indicated by the arrows). Photographing may be carried out with another procedure as long as images of the entire photographing area can be acquired. In FIG. 6, the extending direction of the bridge 1 (floor slab 6) is indicated by x, the direction orthogonal to the x direction in the plane of the floor slab 6 is indicated by y, the direction (vertical downward direction) orthogonal to the floor slab 6 is indicated by z, and the right-handed coordinate system is indicated by (x, y, z).

Figure 7:
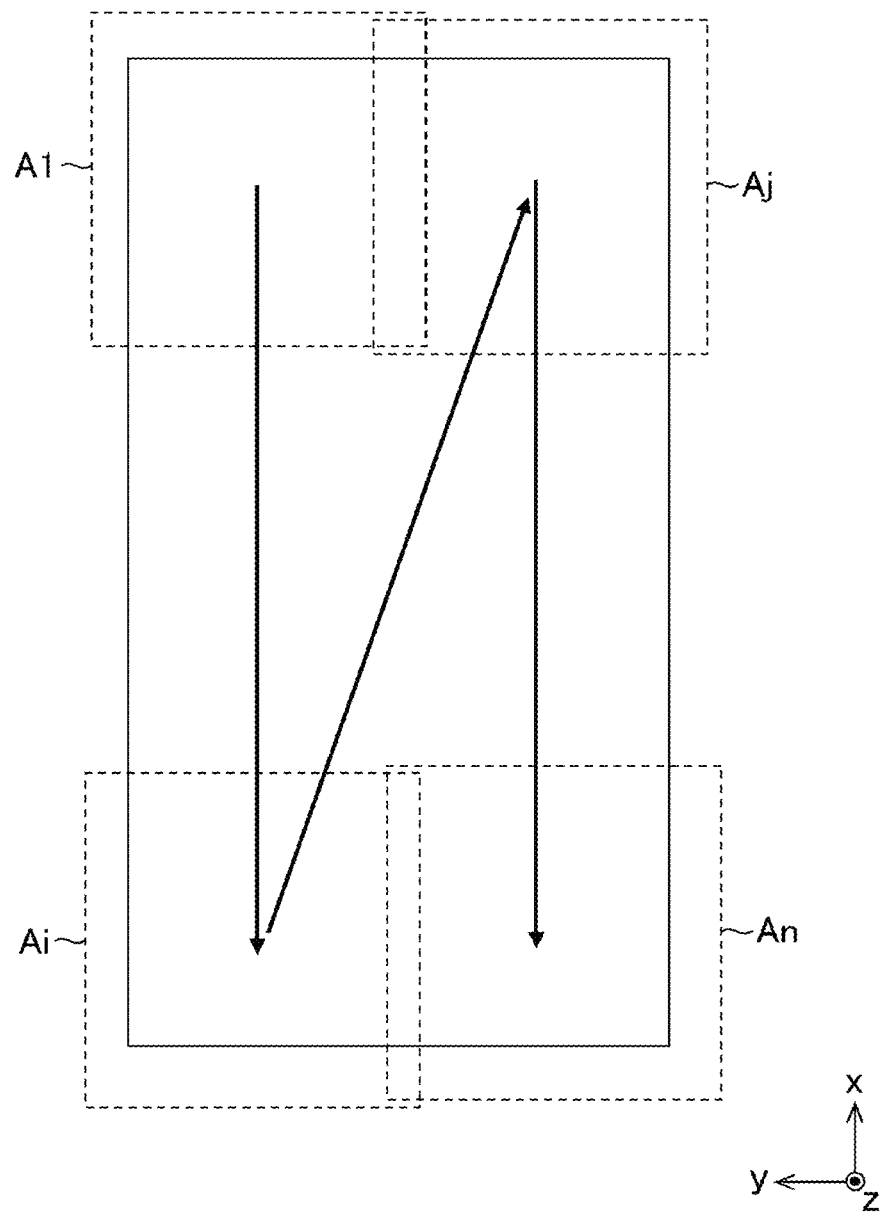
FIG. 7 is a diagram illustrating an example procedure for photographing a panel.

FIG. 7 is a diagram illustrating an example procedure for photographing one panel GO. In the example illustrated in FIG. 7, photographing starts at a region A1 located at an end part on the +x side of the panel GO, and is carried out until the photographing position moves and reaches a region Ai located at an end part in the −x direction. The photographing position again returns to the end part on the +x side, and photographing starts at a region Aj and is carried out until the photographing position reaches a region An at the end part in the −x direction to thereby capture n images (where n is an integer equal to or larger than 2) in total. Photographing may be carried out in a pattern (for example in the order of the regions A1 to Ai and An to Aj) different from the above-described pattern. At the time of photographing, the photographing position may be moved each time one image is captured so as to always capture an image from the front. Alternatively, a plurality of images may be captured from one photographing position while the photographing direction is changed (in this case, images captured in diagonal directions are included). In photographing, it is preferable to appropriately set the photographing position and the photographing direction so that adjacent images sufficiently overlap (for example, about 30%).

Figure 8:
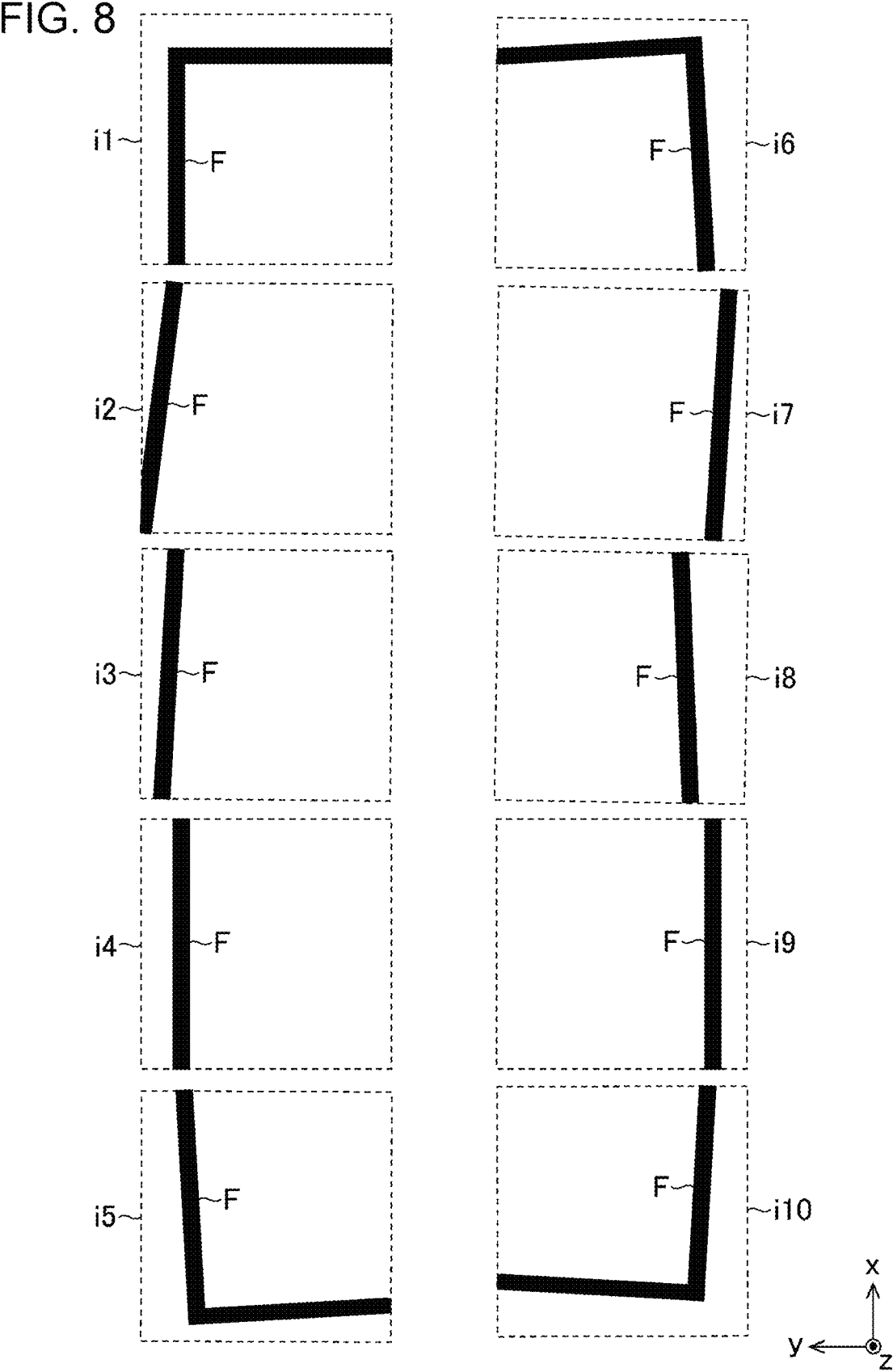
FIG. 8 is a diagram illustrating captured images.

FIG. 8 is a diagram illustrating example captured images (images i1 to i10). FIG. 8 illustrates a frame F of the panel GO (a rectangle defined by the main girders 2 and the cross girders 3) and does not illustrate the other members and damage occurring in the floor slab 6.

Detection of Damage

The damage detection unit 210B detects damage from individual images (images individually forming the plurality of images received in step S100) (step S110: damage detection step). The types of damage include peeling, water leakage, crack, rust, etc. The specific types of damage to be detected may be set in accordance with conditions including the type and characteristics of a structure (photographic subject), the purpose of the inspection, etc. Items to be detected include the position, size, direction, area, shape, etc. The items to be detected may be set in accordance with the types of damage or in accordance with the conditions including the type and characteristics of a structure, the purpose of the inspection, etc. The technique for damage detection is not specifically limited, and various techniques can be used. For example, a method for detecting cracks described in JP4006007B or a method for detecting rust and peeling described in JP2010-538258A can be used. For example, images to which a label stating "this is damage" is attached may be given as teaching data to generate a leaner by machine learning, and the generated leaner may be used to detect damage. Note that a case where cracks are detected and displayed as damage is described below.

In damage detection, the damage detection unit 210B can vectorize a detection result (the result of detection) to represent the detection result by a line segment having the start point and the end point or a set of line segments (in a case of linear damage, such as a crack) or by a figure, such as a polygonal shape, constituted by such line segments (in a case of spreading damage, such as peeling or corrosion). FIG. 9A illustrates an example of a table indicating detection results (before revision and checking), and indicates, for each image, the results of crack detection (the start point and end point, length, width), determination as to whether the image is to be regarded as a check target image, the detection method (whether the crack is detected by the image processing apparatus 10 from the image or revision is made by the user), and whether checking is completed (not completed/completed).

Determination of Check Target Image

The image determination unit 210C determines whether the above-described each individual image is to be regarded as a check target image for which the user is encouraged to check the detection results (step S120: image determination step). The image determination unit 210C can perform determination on the basis of at least one of the image quality of the individual image, the detection results, the photographing conditions, or the construction of the photographic subject, and uses the information stored in the storage unit 220 (see FIG. 4) as necessary. A specific example of determination will be described in detail below.

Display of Image and Detection Results

After an image to be regarded as a check target image has been determined in step S120, the display control unit 210D displays the image and the results of damage detection in the image on the monitor 232 (display device) in association with each other (step S130: display control step). The display is performed for the check target image or a partial image as described below.

Display of Check Target Image or Partial Image

A "partial image" is an image acquired by cutting a partial region from a check target image so as to fit in the display region of the monitor 232 (display device). For example, in a case where the number of pixels (resolution) of a check target image is equal to or smaller than the number of pixels (resolution) of the display region, the display control unit 210D can display the check target image, and in a case where the number of pixels of a check target image exceeds the number of pixels of the display region, the display control unit 210D can cut a part from the check target image as a partial image. FIG. 10 illustrates an example of partial image cutting (an example where six partial images i1A to i1F are cut from the image i1). When a partial region is thus cut from a check target image so as to fit in the display region of the monitor 232 (display device), the number of pixels (resolution) of the displayed image does not decrease, and a situation where it is difficult to check (or it is not possible to check) damage due to a reduced image is unlikely to occur. Accordingly, the user can precisely check and revise the detection results.

Display Patterns for Image and Detection Results

The display of the image and detection results in step S130 can be performed with, for example, the following patterns.

Display Pattern 1

Figure 11:
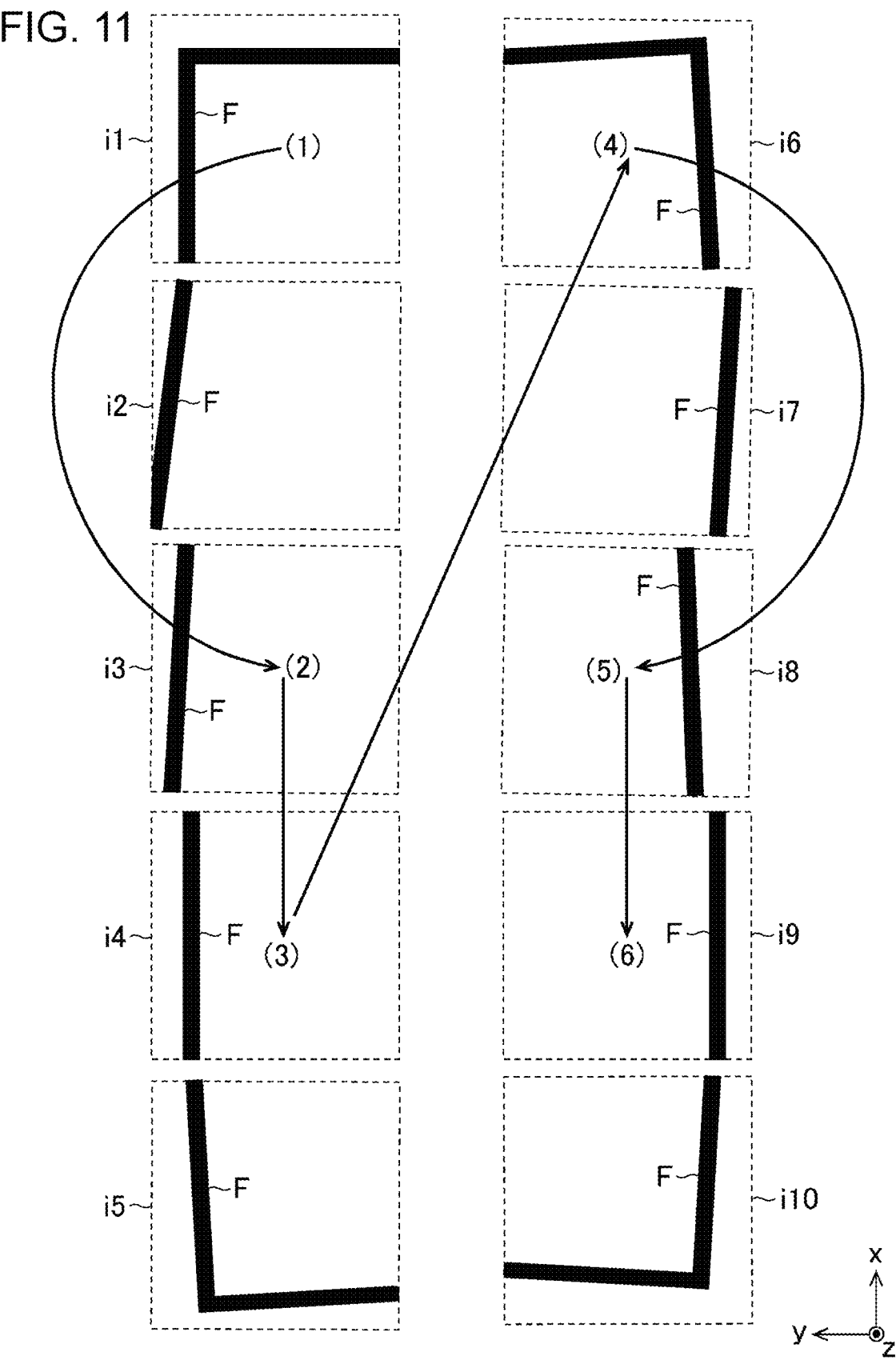
FIG. 11 is a diagram illustrating an example order in which images are displayed.
Figure 12:
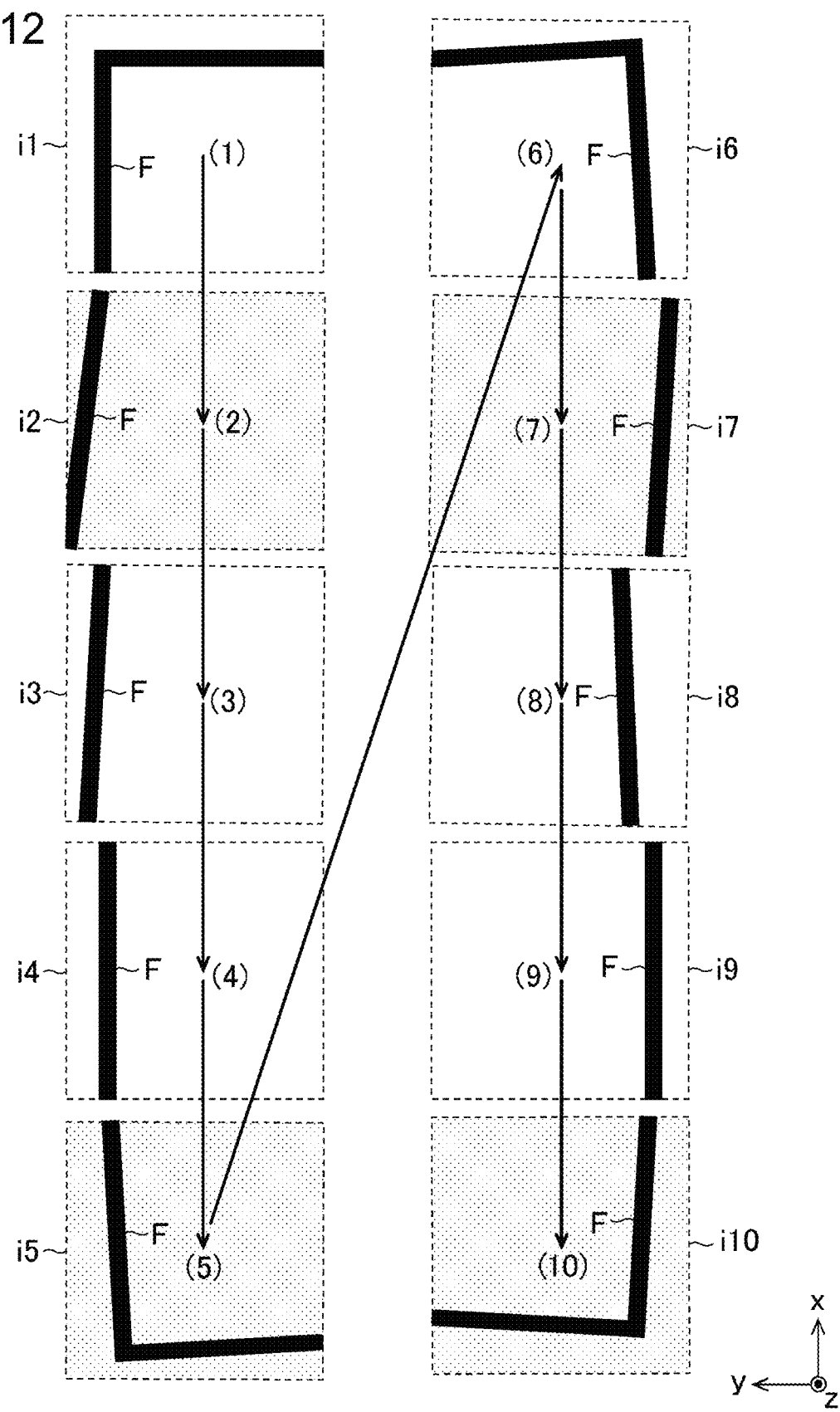
FIG. 12 is a diagram illustrating another example order in which images are displayed.

In a display pattern 1, the display control unit 210D displays only an image that is determined "to be a check target image" and the detection results. For example, in FIG. 11, the display control unit 210D displays the images i1, i3, i4, i6, i8, and i9 (it is assumed that these images are determined to be "check target images") and the detection results for these images in association with each other. The display control unit 210D does not display (but skip) the images i2, i5, i7, and i10 (non-check target images, namely, images that are not check target images among the plurality of images acquired by photographing the photographic subject) or the detection results. Note that FIG. 11 and FIG. 12 described below are diagrams that indicate the order in which the images are displayed, and the results of damage detection are not illustrated. In FIG. 11 and FIG. 12, each numeral in parentheses indicates the order in which the images are displayed. Specific examples of displaying images and detection results will be described below.

Display Pattern 2

In a display pattern 2, the display control unit 210D displays not only an image that is determined to be a check target image but also an image that is a non-check target image together with the detection results. The display control unit 210D displays anon-check target image so as to be distinguishable from a check target image and its detection results. For example, as illustrated in FIG. 12, the display control unit 210D displays the images i1 to i10 (all images) and the detection results (not illustrated in FIG. 12) for the images in association with each other such that the images i2, i5, i7, and i10 (non-check target images) are grayed out (an example of distinguishable display). Instead of the gray-out display, the display control unit 210D may perform distinguishable display by adding a character, a numeral, a figure, a symbol, etc. or by coloration, etc.

With the above-described display patterns 1 and 2, an image (check target image) for which the detection results are to be checked is distinctively displayed, and a detection result for the check target image is revised on the basis of an instruction input by the user. Accordingly, the time taken for checking and revision can be reduced. The details of revision of a detection result will be described below.

Example Screen Display of Image and Detection Results

Figure 13:
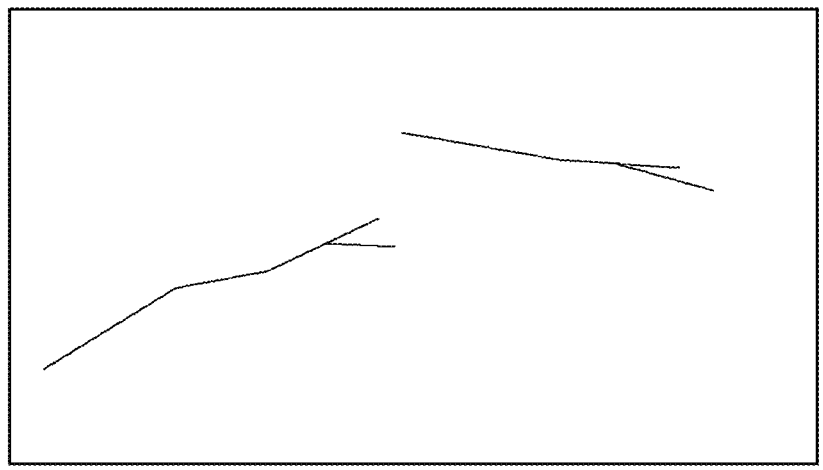
FIG. 13 is a diagram illustrating cracks appearing in a floor slab.
Figure 14:
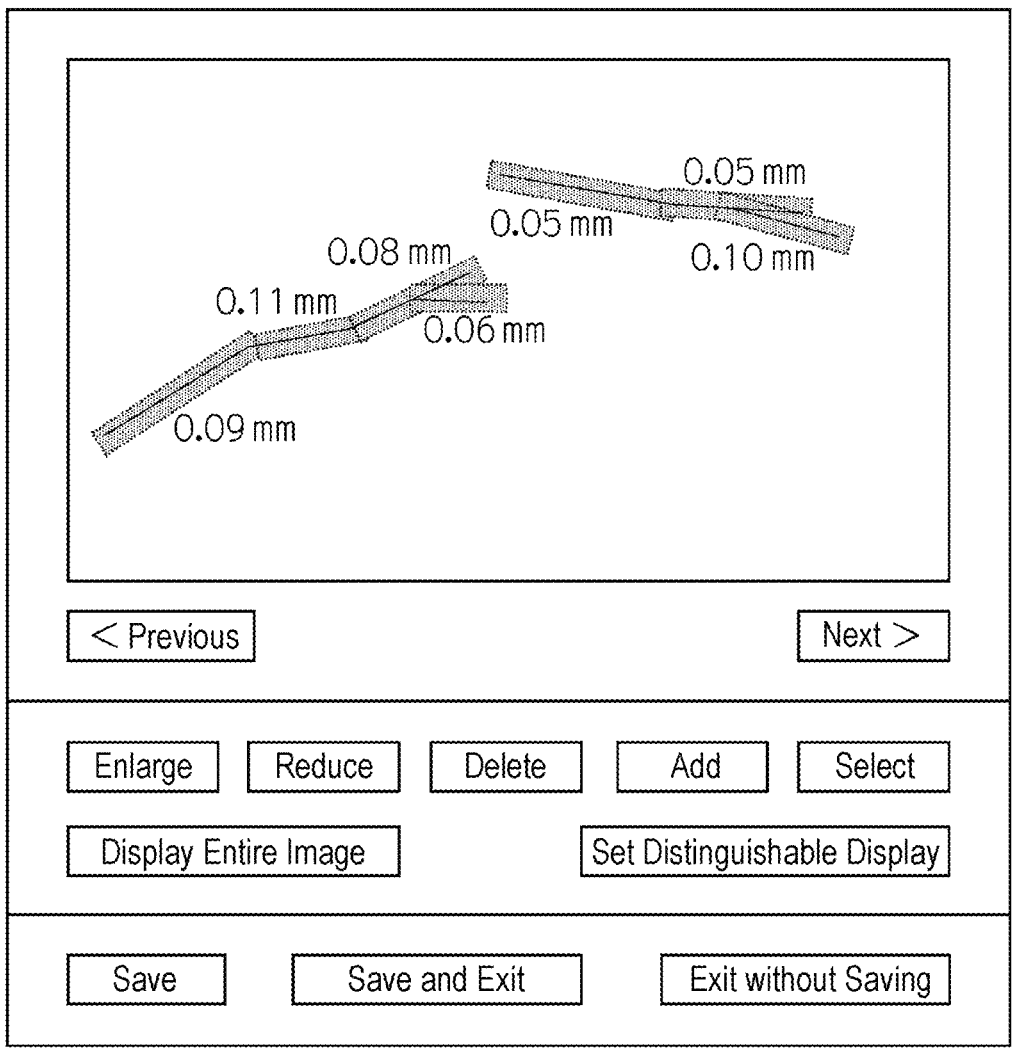
FIG. 14 is a diagram illustrating a state of screen display of a check target image.

In a situation where cracks (damage) appear as illustrated in FIG. 13, example screen display where an image and the results of crack detection are displayed in association with each other is illustrated in FIG. 14. In the example illustrated in FIG. 14, the display control unit 210D superimposes and displays colored bold lines (rectangles) on the crack parts in the image, and further displays numeric values indicating the widths of the cracks to thereby associate the image and the detection results with each other (note that the numeric display of widths will be omitted in the subsequent figures). The image and the detection results can be associated with each other by using characters, numerals, figures, symbols, colors, etc. in accordance with the detection results as in the example illustrated in FIG. 14. The brightness and/or saturation of coloration may be changed in accordance with the degree of damage (the length, width, etc. of the crack). The display control unit 210D may turn the superimposed display and the display of widths on and off in accordance with an instruction given by the user via the operation unit 240. In FIG. 14, text displayed in each rectangle (for example, "Set Distinguishable Display") represents a button for performing a process corresponding to the text. When each button is specified, the process displayed by the button is performed as described below.

Successive Display of Images and Detection Results

Figure 15A:
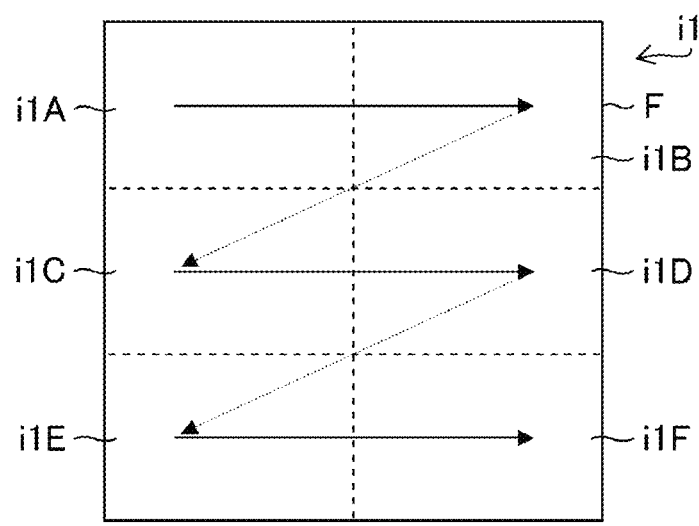
FIGS. 15A to 15C are diagrams illustrating states of distinguishable display of partial images.

In FIG. 14, when the user specifies the "Previous" or "Next" button, the display control unit 210D displays the previous check target image and its detection results or the next check target image and its detection results. At this time, in a case where partial images are cut from the check target image, the display control unit 210D displays the previous partial image and its detection results or the next partial image and its detection results. FIG. 15A illustrates an example order in which partial images in the image i1 (check target image) are displayed, and the partial images i1A to i1F are displayed in this order (the detection results are not illustrated). After the detection results for all regions of one check target image have been checked and/or revised, the display control unit 210D displays another check target image and the detection results (steps S150 and S160 in FIG. 5). Therefore, the possibility of omission in checking can be reduced. In a case where, for example, "Next", "Save", or "Save and Exit" is specified in the display illustrated in FIG. 14, the processing unit 210 (detection result revising unit 210F) can determine that "the detection results for the image that is being displayed have been checked and/or revised (an instruction indicating that the user has checked and/or revised the detection results is input)". The detection result revising unit 210F adds a flag indicating "check completed" to the checked image (see FIG. 9B).

Display of Entire Image

Figure 15B:
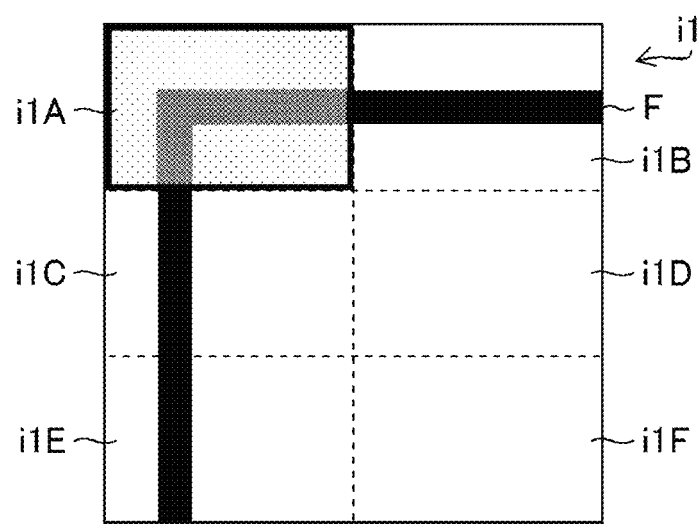
Figure 15C:
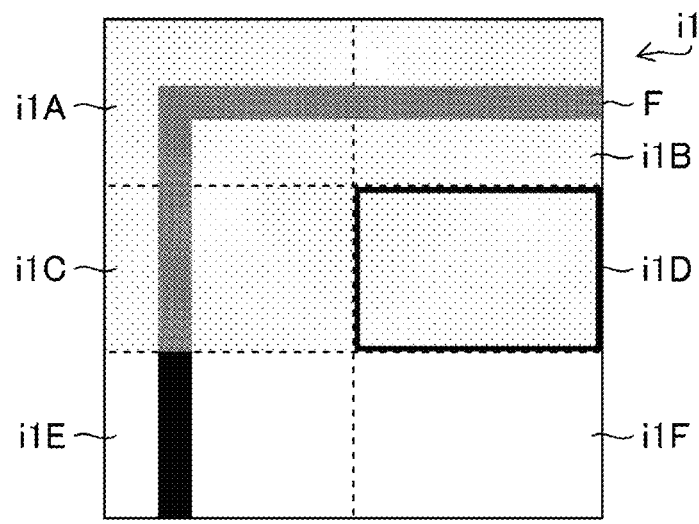

When the user specifies the "Display Entire Image" button in FIG. 14, the display control unit 210D displays the entire check target image and a region occupied by a partial image in the check target image. For example, when the "Display Entire Image" button is specified in a state where the partial image i1A is displayed, the entire image i1, which is the check target image, is displayed, and the partial image i1A that is currently displayed is grayed out in the image i1 as illustrated in FIG. 15B. The gray-out display is an example of distinguishable display, and distinguishable display may be performed by adding a character, a numeral, a figure, a symbol, etc. or by coloration, etc. The display may be performed in a window separate from the display as illustrated in FIG. 14. As illustrated in FIG. 15C, regions for which the detection results have already been checked and/or revised may be grayed out (an example of distinguishable display). With such display, the user can easily grasp the state of checking and/or revision and efficiently perform operations. Note that detection results are checked on a check target image or a partial image, and this image is displayed without reduction. Therefore, in a case of displaying the entire image, the image may be reduced as necessary (for example, in a case where the number of pixels of the entire image is larger than the number of display pixels of the monitor 232).

Display of Specified Region

Figure 16:
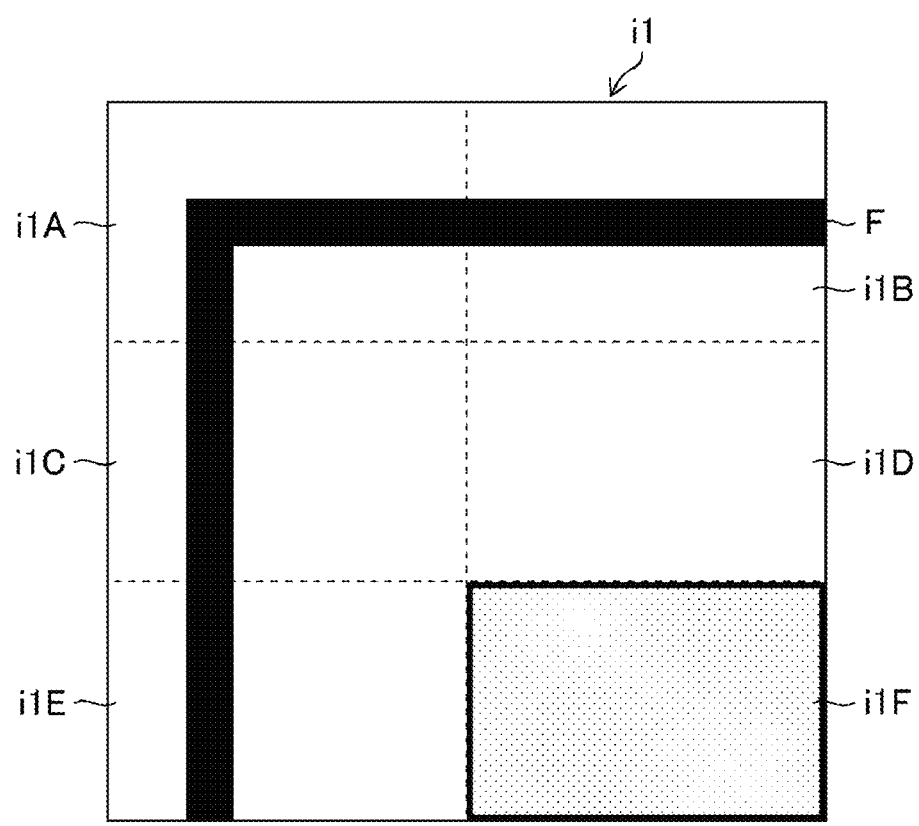
FIG. 16 is a diagram illustrating a state where an image is specified.

As in the above-described example, when the user specifies a region in a check target image in a state where the check target image is displayed, the display control unit 210D displays a partial image that corresponds to the specified region and the detection results for the partial image as illustrated in FIG. 14. For example, when the user specifies the partial image i1F in the image i1 as illustrated in FIG. 16, the display control unit 210D displays the partial image i1F and the detection results for the partial image i1F as illustrated in FIG. 14. Accordingly, the user can check the detection results for the desired region.

Revision of Detection Result

The detection result revising unit 210F revises a detection result on the basis of an instruction input by the user via the operation unit 240 (step S140: detection result revising step). As "revision" of a detection result, for example, addition (adding information about damage that is omitted in detection), correction (correcting an incorrect detection result to a correct result), and deletion (deleting information about damage that is erroneously detected) can be made. It is assumed that, at the time of revision, the check target image is displayed on the screen as illustrated in FIG. 14.

Addition for Omission in Detection

Figure 17A:
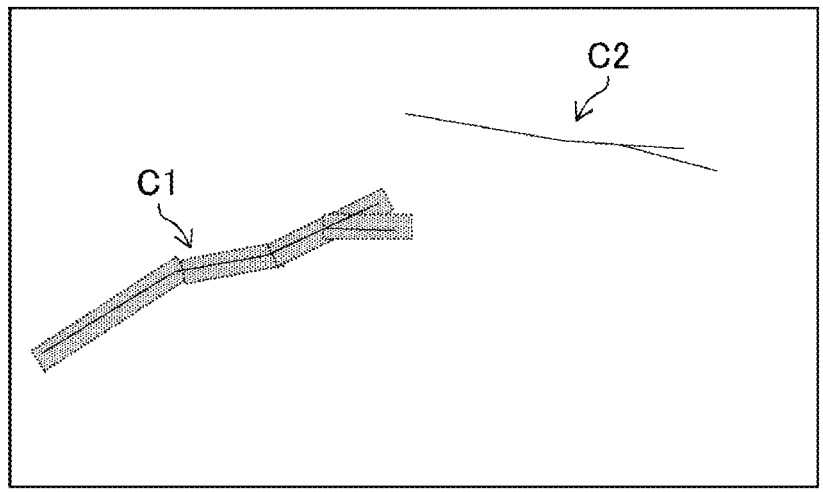
FIGS. 17A and 17B are diagrams illustrating a state where revision is made to omission in damage detection.
Figure 17B:
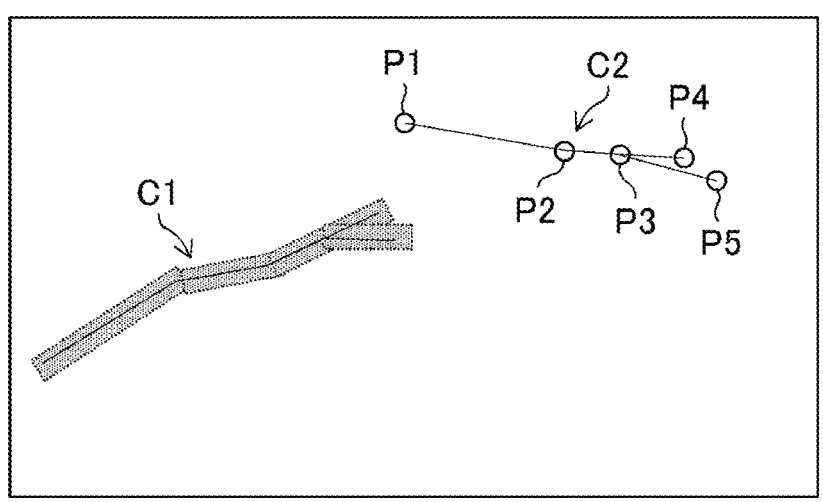

FIGS. 17A and 17B are diagrams illustrating example revision (addition) made to omission in detection. FIG. 17A illustrates a state where a crack C1 is detected (a bold line is superimposed) but a crack C2 is omitted in detection (a bold line is not superimposed). In this case, the user specifies "Add" in the screen display as illustrated in FIG. 14 and subsequently specifies the start point and the end point of each crack (points P1 to P5) by clicking the mouse 244 as illustrated in FIG. 17B. The detection result revising unit 210F adds the crack in accordance with this operation. FIG. 9B illustrates an example indicating a state where a crack having an ID R001-3-2 has been added (a state after checking and revision). In this case, the length of the crack can be calculated from the start point and the end point. The user can visually measure the width and input the width using the keyboard 242. When the user visually measures the width of a crack, the display control unit 210D and/or the detection result revising unit 210F may display an image of a marker that serves as an indicator for measurement (for example, an image including a plurality of line segments having thicknesses that correspond to the actual widths of cracks). Alternatively, for example, the construction information acquisition unit 210E may acquire information about the size of the panel, the size per one pixel, etc. (the construction information acquisition unit 210E can use the construction information 220D and the photographing conditions 220B), and the damage detection unit 210B may convert the result of visual measurement to an actual size to calculate the length, width, etc. of the crack.

Deletion of Erroneous Detection

Figure 18A:
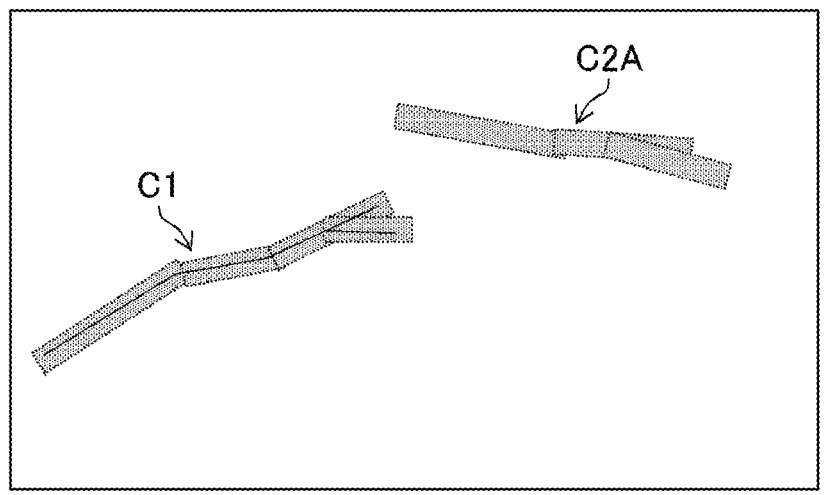
FIGS. 18A and 18B are diagrams illustrating a state where revision is made to erroneous damage detection.
Figure 18B:
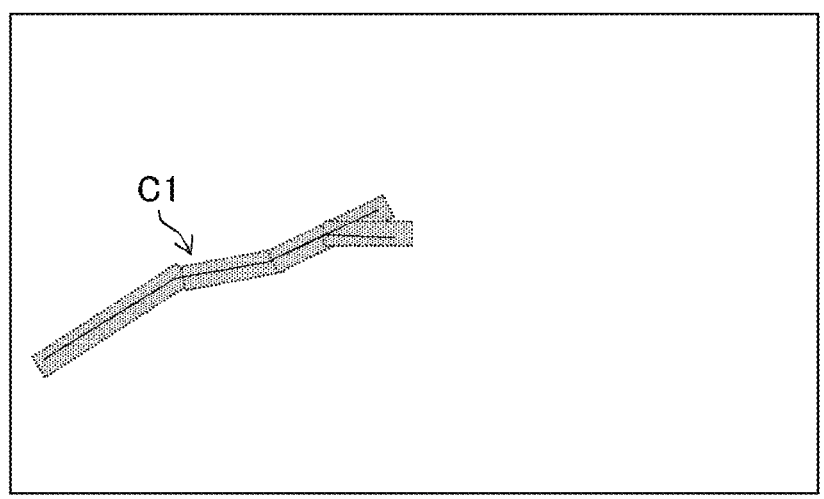

FIGS. 18A and 18B are diagrams illustrating example revision (deletion) made to erroneous detection. FIG. 18A illustrates a state where a crack C2A that is not present is erroneously detected. In this case, the user specifies "Delete" in the screen display as illustrated in FIG. 14 and selects the crack C2A. Then, the selected crack is deleted as illustrated in FIG. 18B. The detection result revising unit 210F deletes the crack from the list of detection results (see FIGS. 9A and 9B) in accordance with this operation.

Correction of Incorrect Detection Result

In addition to addition and deletion, an incorrect detection result can be corrected. For example, in a case of correcting the width of a crack, the user uses "Select" on the screen display as illustrated in FIG. 14 to specify a detection result that the user wants to correct, and inputs a correct width. The detection result revising unit 210F corrects the detection result in accordance with the input operation (see FIGS. 9A and 9B). Also in the case of correction, the result of visual measurement may be converted to the actual size as in the case of addition.

After the detection results have been checked and/or revised for all regions (all partial images) of one check target image, the display control unit 210D displays another check target image and the detection results for the other check target image. That is, in a case of YES in step S150, the flow proceeds to step S160, and the process (display and checking and/or revision) is repeated for the other image.

Determination of Check Target Image

In step S120 in FIG. 5, the image determination unit 210C determines whether an individual image is to be regarded as a check target image on the basis of at least one of the image quality of the individual image, the detection results, the photographing conditions, or the construction of the photographic subject. For example, the image determination unit 210C can perform determination on the basis of at least one of the items described below.

Determination of Image Quality Using Machine Learning

Image quality may be determined by using the results of machine learning (deep learning, etc.). For example, each time a new image is stored in the storage unit 220 (or each time a new image is captured), the image determination unit 210C performs an image analysis process using deep learning on the basis of a deep learning algorithm to analyze the image quality and configure an image quality evaluator. The deep learning algorithm is a publicly known convolution neural network technique, that is, an algorithm for determining the image quality through repetition of a convolution layer and a pooling layer, a fully connected layer, and an output layer. Whether to "perform such machine learning" and/or whether to "use the results of learning" may be set by a user operation via the operation unit 240. The image determination unit 210C can determine the image quality on the basis of the result of evaluation using the image quality evaluator and determine an image that is determined to have "poor image quality" (for example, "the evaluated value is smaller than a threshold") to be a check target image.

Determination Based on Spatial Frequency Spectrum

Image quality can be quantified with the maximum spectrum value, the average spectrum value, the sum of spectra, etc. in a high-frequency range in the spatial frequency spectrum of a region in the image. Specifically, as the maximum value, the average value, or the sum for components within a radius of a specific number of pixels (r pixel radius) from the four corners of a spatial frequency spectrum image (which is acquired by performing a fast Fourier transform (FFT) on the captured image) is larger, high-frequency components are stronger (a larger number of high-frequency components are present), and therefore, blurring occurs to a smaller degree and the image quality is better. The image determination unit 210C does not regard an image having such good image quality as a check target image and can determine an image having weak (small number of) high-frequency components and having poor image quality to be a check target image.

Determination Based on Histogram

Figure 19:
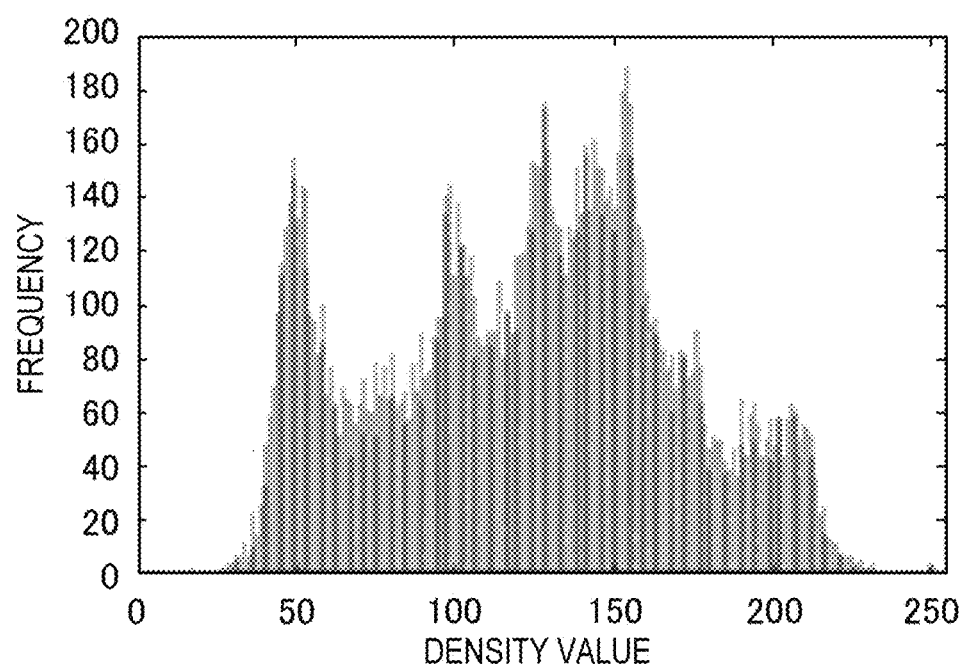
FIG. 19 is a diagram illustrating an example histogram.

In determination based on a histogram (an example indicator indicating image quality), the image determination unit 210C converts an individual image (a color image formed of R, G, and B components) to a gray-scale image. For example, the following holds: Gray scale (density)=R× 0.30+G×0.59+B×0.11 (where R, G, and B are values of the red, green, and blue signals respectively). The image determination unit 210C calculates a histogram (density histogram, see the example in FIG. 19) of the gray-scale image obtained as a result of conversion. The calculation of the histogram and determination described below may be performed for a partial region instead of the entire individual image. The image determination unit 210C uses G(i) {i=0, 1, . . . , 255} as a histogram of each density value (the image is darker as the value is closer to 0 and brighter as the value is closer to 255) and determines whether the individual image is too bright or too dark using expressions (1) and (2) below. Thresholds (kb, hb, kd, and hd) for determination may be default values (for example, kb=205, hb=0.5, kd=50, and hd=0.5) or may be set by the image determination unit 210C in accordance with user input via the operation unit 240.

$$\frac{\sum_{j=kb}^{255} G(j)}{\sum_{i=0}^{255} G(i)} \geq hb \quad (1)$$

$$\frac{\sum_{j=0}^{kd} G(j)}{\sum_{i=0}^{255} G(i)} \geq hd \quad (2)$$

In a case where the ratio of density values equal to or larger than kb to all density values is equal to or larger than hb in expression (1) described above, the image determination unit 210C determines the individual image to be "too bright". In this case, the image determination unit 210C determines that "the image quality is low (because the image is too bright)" and regards the individual image as a check target image. Similarly, in a case where the ratio of density values equal to or smaller than kd to all density values is equal to or larger than hd in expression (2), the image determination unit 210C determines that "the image quality is low (because the image is too dark)" and regards the individual image as a check target image.

On the basis of the histogram, it is possible to also determine whether gradations are lost. For example, the image determination unit 210C uses G(i) {i=0, 1, . . . , 255} as a histogram of each density value and determines that "gradations on the shadow side are lost" in a case of G(0)>Td and that "gradations on the highlight side are lost" in a case of G(255)>Tb. In these cases, the image determi-nation unit 210C determines that "the image quality is low" and regards the individual image as a check target image. The thresholds (Td and Tb) for determination may be default values (for example, Td=0 and Tb=0) or may be set by the image determination unit 210C in accordance with user input via the operation unit 240.

Determination Based on Degree of Certainty of Detection Result

The damage detection unit 210B may calculate the degree of certainty of a detection result (for example, the degree of certainty indicating that detected damage is actual damage) and perform determination and/or distinguishable display on the basis of the degree of certainty. For example, an image in which the number of detection results having a high degree of certainty is large and/or the density thereof is high has a reduced need for checking, and therefore, the display control unit 210D possibly performs distinguishable display (adding a character, a numeral, a figure, or a symbol or by coloration, etc.) at the time of display to indicate that checking is not necessary. On the other hand, an image in which the number of detection results having a low degree of certainty is large and/or the density thereof is high is in great need for checking, and therefore, it is preferable to display the image as a check target image as illustrated in FIG. 14. Note that when one or more thresholds are set for the degree of certainty and the number and/or density of detection results, and a comparison of the detection results is performed on the basis of the thresholds, determination of distinguishable display, etc. can be performed. In a case of performing the process using the degree of certainty, a column for the degree of certainty may be provided in the list of detection results (see FIGS. 9A and 9B). In the process as described above, the damage detection unit 210B sets thresholds for the feature values (for example, the length and width of a crack, the space between cracks, the density of cracks, etc.) for each type of damage and adds up weighting coefficients calculated in accordance with the relationships between the detection results and the thresholds (whether a detection result is within the range of a threshold, and in a case where the detection result is outside the range, to what degree the detection result goes outside the range) for all feature values. Accordingly, the degree of certainty can be calculated. However, calculation of the degree of certainty is not limited to this form.

Figure 20A:
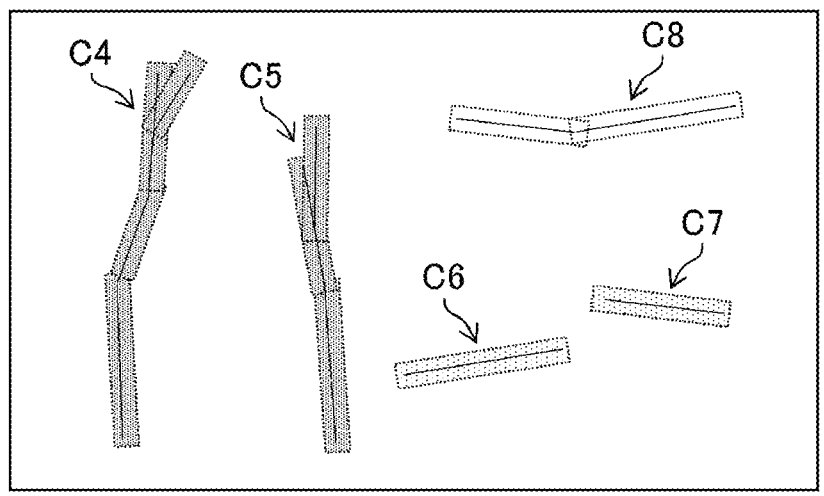
FIGS. 20A and 20B are diagrams illustrating example display in accordance with the degrees of certainty of detection results.
Figure 20B:
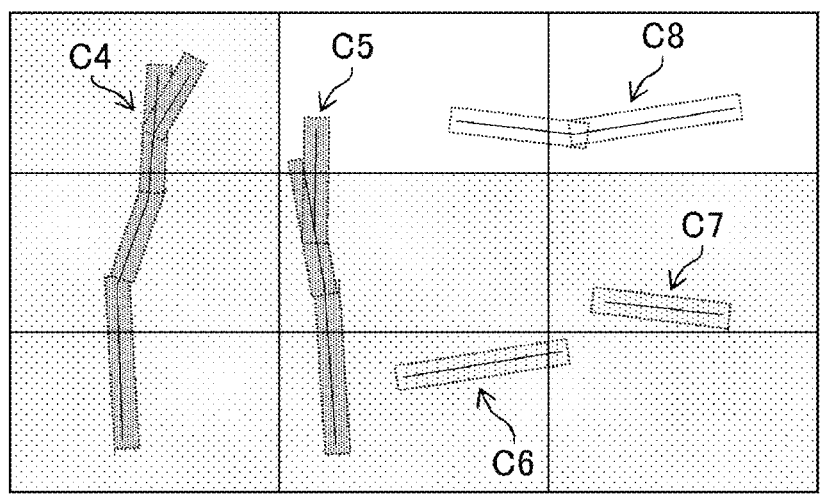

For example, as illustrated in FIG. 20A, the display control unit 210D may perform coloration display (an example of distinguishable display) for cracks in accordance with the degree of certainty. For example, a form is possible in which a detection result having a high degree of certainty (equal to or larger than a first threshold) is colored red, a detection result having a medium degree of certainty (equal to or larger than a second threshold and smaller than the first threshold) is colored yellow, and a detection result having a low degree of certainty (smaller than the second threshold) is made colorless. FIG. 20A does not illustrate different colors but shades of gray (a detection result in darker gray has a higher degree of certainty) for convenience sake. Degrees of certainty can be classified into two levels (high/low), three levels (high/medium/low), or more than three levels, and the types of coloration or shading based on the number of levels can be set (in FIG. 20A, the degrees of certainty are classified into three levels). As illustrated in FIG. 20B, regions in which only detection results having a high degree of certainty (cracks C4, C5, C6, and C7 each having a "high" or "medium" degree of certainty in the three levels) are present may be grayed out to indicate that checking is not necessary. The gray-out display is an example of distinguishable display, and distinguishable display may be performed by adding a character, a numeral, a figure, or a symbol or by coloration, etc.

Determination Based on Features of Detection Result

Discontinuous cracks, short cracks, thin cracks, etc. may result from omission in detection or erroneous detection. Accordingly, the display control unit 210D may display such discontinuous cracks, etc. in a distinguishable manner. Further, the image determination unit 210C determines that an image in which such cracks are present is to be regarded as a check target image so as to allow the user to efficiently check the detection results. For example, in a case where an end point (the start point or the end point) of a crack is present within an area that includes a predetermined number of pixels (for example, 50 pixels) around an end point of another crack or within a predetermined distance (for example, 20 mm) from another crack, the image determination unit 210C can determine that "a discontinuous crack appears, and therefore, this image is to be regarded as a check target image". The image determination unit 210C can acquire information about the size of the panel, the size per one pixel, etc. (the image determination unit 210C can use the construction information 220D and the photographing conditions 220B) and perform conversion to the actual size to thereby determine a short crack and a thin clock.

Figure 21A:
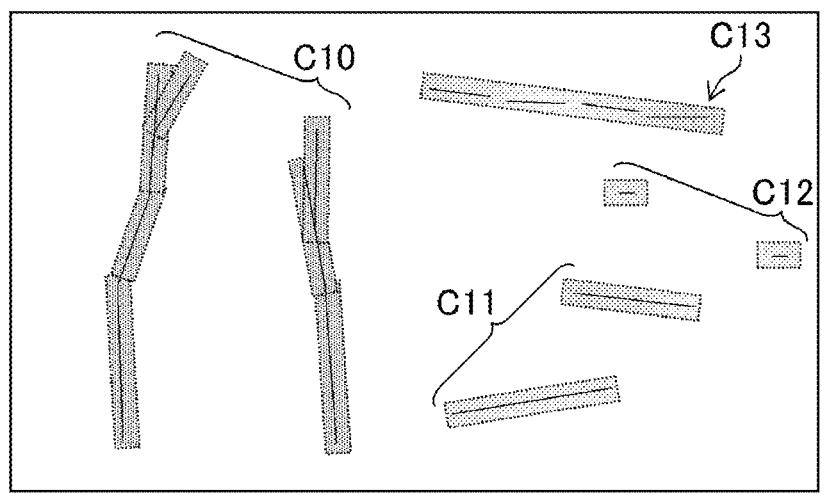
FIGS. 21A and 21B are diagrams illustrating example display in accordance with the features of detection results.
Figure 21B:
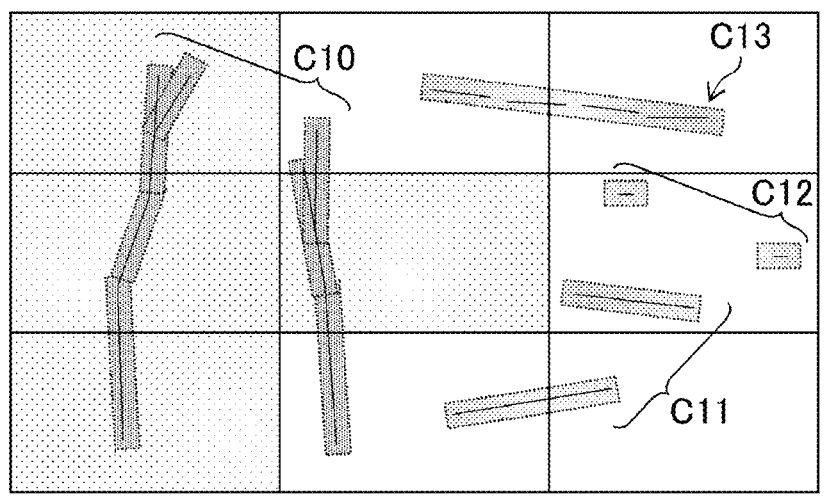

FIGS. 21A and 21B are diagrams illustrating example distinguishable display based on the features of detection results. In FIG. 21A, the display control unit 210D colors a continuous crack and a thick crack (crack C10) dark and colors a thin crack, a short crack, and a discontinuous crack (cracks C11, C12, and C13) light. FIG. 21B illustrates an example where regions in which only a continuous crack or a thick crack is present, that is, regions having a reduced need for checking, are grayed out. The gray-out display is an example of distinguishable display, and distinguishable display may be performed by adding a character, a numeral, a figure, or a symbol or by coloration, etc. With such distinguishable display, the user can efficiently check the results of damage detection.

Determination Based on Photographing Conditions

Figure 22A:
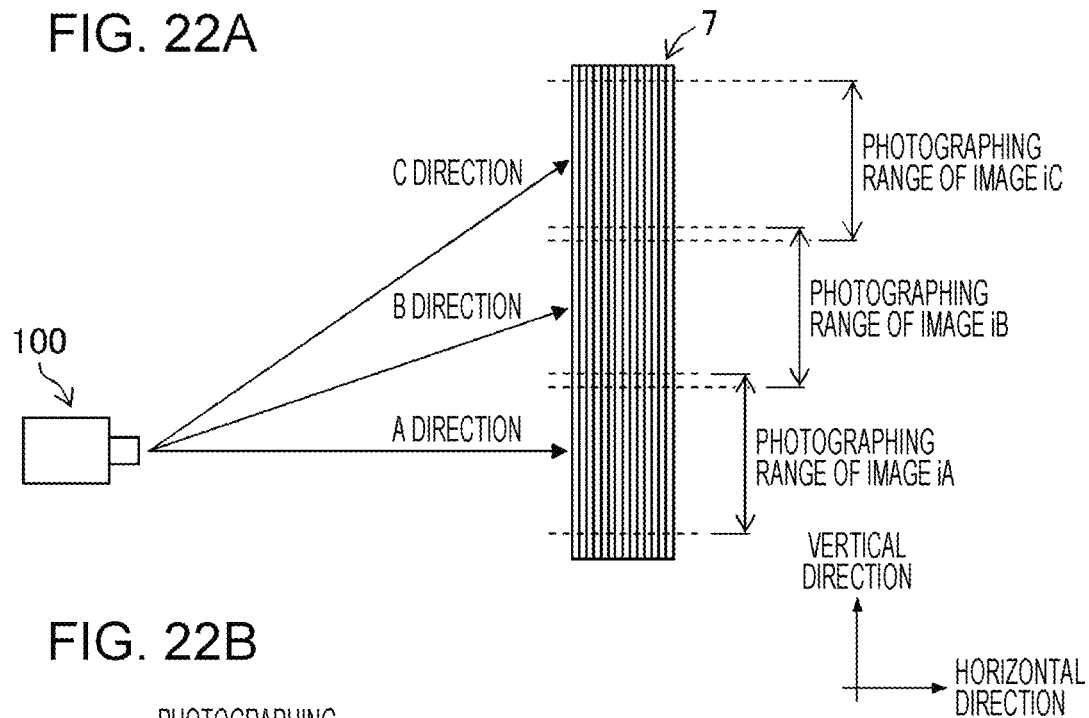
FIGS. 22A and 22B are diagrams illustrating states of photographing while changing the photographing direction.
Figure 22B:
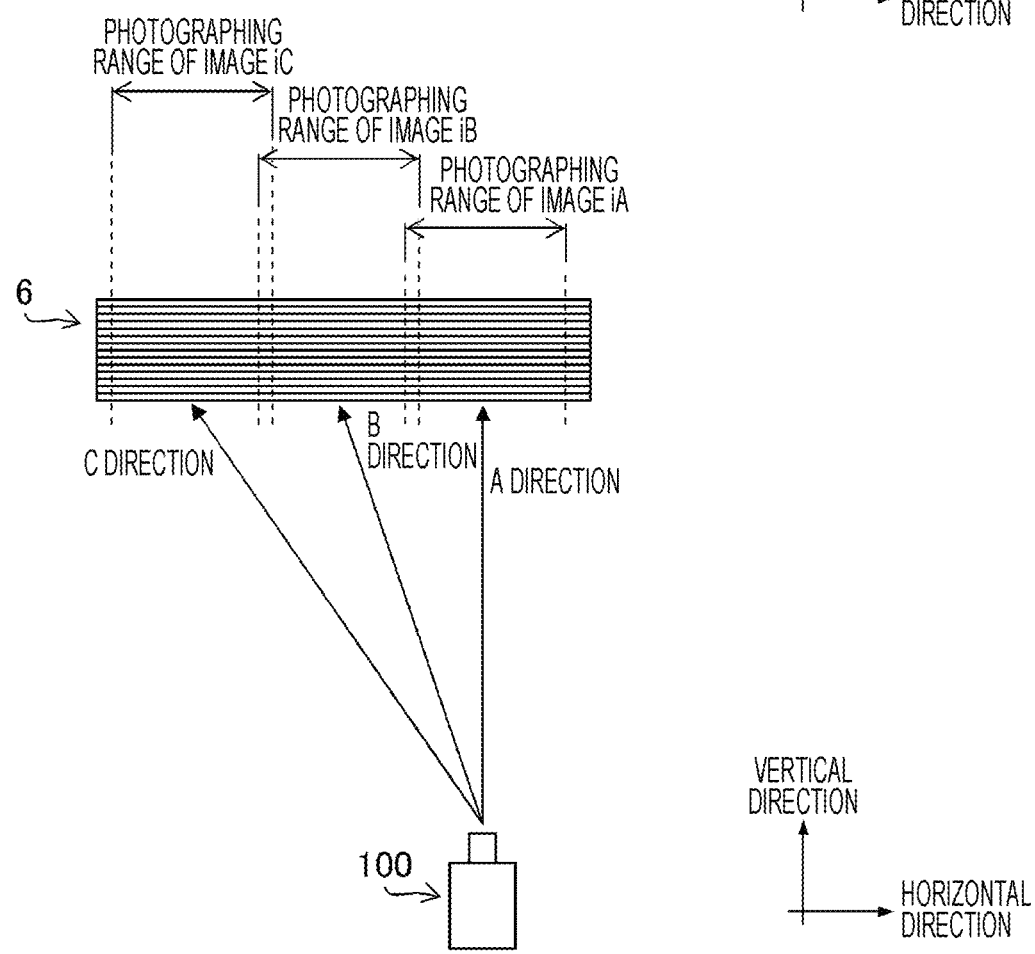

In an image acquired by photographing a photographic subject, a region away from the in-focus position in an angle change direction relative to the photographic subject is outside the range of the depth of field and is blurred. Such a problem is significant in a case where a wide area is photographed from one photographing position while the photographing direction is changed (pan, tilt, etc.). For example, as illustrated in FIG. 22A, in a case where the photographing position of the digital camera 100 is fixed, and the pier 7 is photographed while the photographing direction is changed upward and downward (in the vertical direction), any of the end parts in the up-down direction or both sides are blurred in an acquired image (in a case where the center of the image is in focus, both sides are blurred, and in a case where the in-focus position is on the upper side or lower side of the image, the lower side or upper side is blurred). Such a blurred region becomes wider as the photographing angle (the angle from the front direction) becomes wider. For example, in an image iA captured in A direction (front direction), a blurred region is narrow, and in an image iB captured in B direction, any of the end parts in the up-down direction or both sides are blurred. In an image iC captured in C direction, a blurred region is wider than that in the image iB. Such a situation similarly occurs in a case where, for example, the floor slab 6 is photographed from one photographing position while the photographing direction is changed in the horizontal direction (forward and backward and/or rightward and leftward) as illustrated in FIG. 22B.

The image determination unit 210C can determine an image that includes such a blurred region (a region outside the range of the depth of field) to be a check target image, and the display control unit 210D can display the in-focus region and/or the blurred region in a distinguishable manner. Distinguishable display can be performed by adding different characters, numerals, figures, symbols, colors, etc. to the in-focus region and the blurred region or changing the degrees thereof. Distinguishable display may be applied to any one of the regions (for example, the in-focus region may be grayed out), or distinguishable display may be applied to both regions. Accordingly, the user can easily distinguish a region in which erroneous detection, omission in detection, etc. is likely to occur, and can efficiently check and/or revise the results of damage detection. Note that it is preferable to store in advance the relationship between the photographing angle and the blurred region in the storage unit 220 as a database.

Determination Based on Amount of Focus Shift

Figure 23:
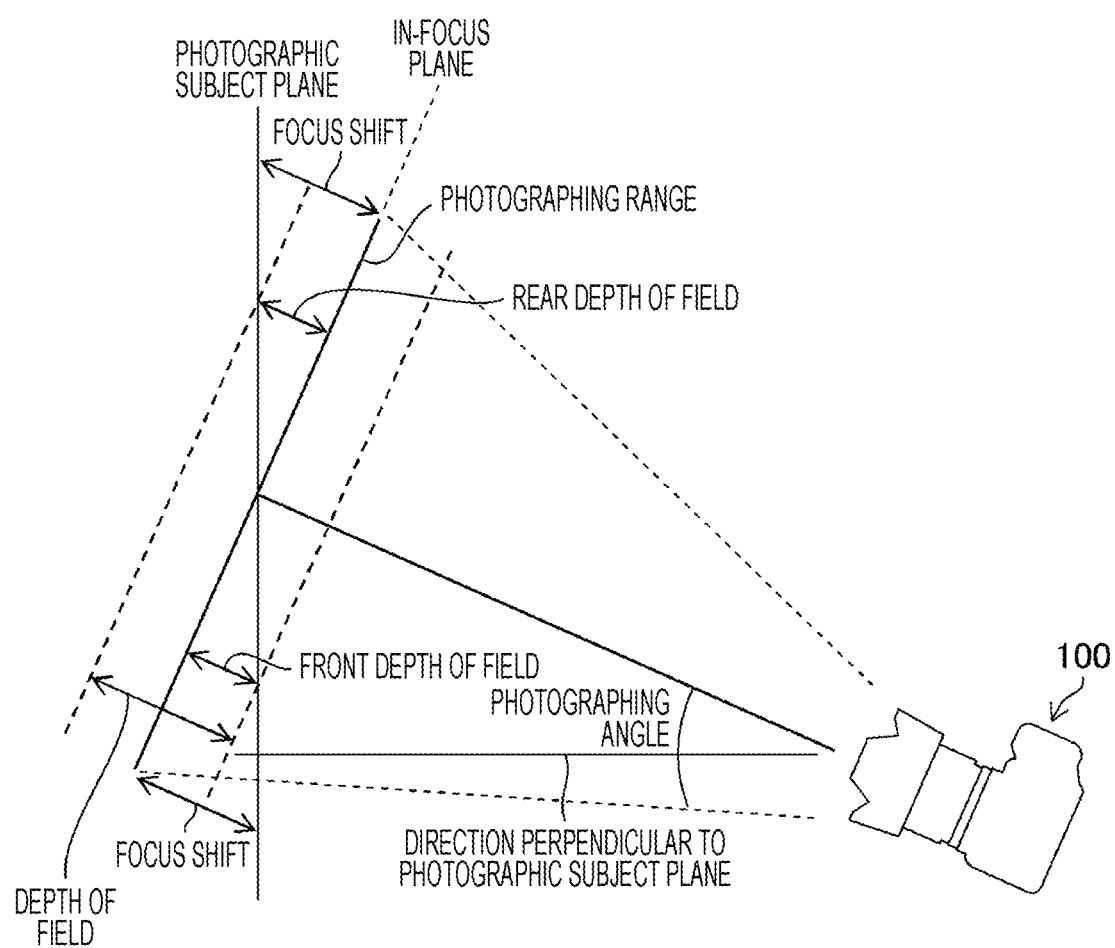
FIG. 23 is a diagram illustrating a state where a focus shift occurs.

As illustrated in FIG. 23, in a case where the photographing angle is performed with the camera 100 tilted, the direction of the photographic subject plane and the direction of the in-focus plane differ, resulting in a focus shift. When this focus shift exceeds the depth of field, blurring occurs. The display control unit 210D can display a region having an amount of focus shift that is within the range of the depth of field in the image and/or a region having an amount of focus shift that is outside the range of the depth of field in the image in a distinguishable manner. The image determination unit 210C can determine an image that includes a region having an amount of focus shift that exceeds the range of the depth of field to be a check target image. The display control unit 210D can display a region within the range of the depth of field and a region outside the range thereof in a distinguishable manner by adding different characters, numerals, figures, symbols, colors, etc. or changing the degrees thereof. Distinguishable display may be applied to any one of the regions (for example, the region within the depth of field may be grayed out), or distinguishable display may be applied to both regions. Accordingly, the user can easily distinguish a region (a region having an amount of focus shift that exceeds the range of the depth of field) in which erroneous detection, omission in detection, etc. is likely to occur, and can efficiently check and/or revise the results of damage detection. A region that is blurred due to a focus shift appears in both end parts in the up-down direction in a case where the in-focus position is at the center of the image, appears on the lower side in a case where the in-focus position is on the upper side of the image, and appears on the upper side in a case where the in-focus position is on the lower side of the image.

The depth-of-field calculation unit 211 can calculate the depth of field using expressions (3) to (5) below.

$$\text{Front depth of field (mm)} = \frac{\{\text{Permissible circle of confusion diameter (mm)} \times \text{Aperture value} \times \text{Subject distance (mm)}^2\}}{\{\text{Focal length (mm)}^2 + \text{Permissible circle of confusion diameter (mm)} \times \text{Aperture value} \times \text{Subject distance (mm)}\}} \quad (3)$$

$$\text{Rear depth of field (mm)} = \frac{\{\text{Permissible circle of confusion diameter (mm)} \times \text{Aperture value} \times \text{Subject distance (mm)}^2\}}{\{\text{Focal length (mm)}^2 - \text{Permissible circle of confusion diameter (mm)} \times \text{Aperture value} \times \text{Subject distance (mm)}\}} \quad (4)$$

Depth of field (mm)=Front depth of field (mm)+Rear
  depth of field (mm)              (5)

Note that in expressions (3) to (5), the permissible circle of confusion diameter is equal to the pixel size of the imaging element. The photographing range in the longitudinal direction and that in the lateral direction can be calculated using expressions (6) and (7) below.

Photographing range (longitudinal direction)=Subject
  distance×Sensor size (longitudinal direction)/
  Focal length               (6)

Photographing range (lateral direction)=Subject distance×Sensor size (lateral direction)/Focal
  length                 (7)

Determination Based on Blurring Due to Curvature of Field

Figure 24A:
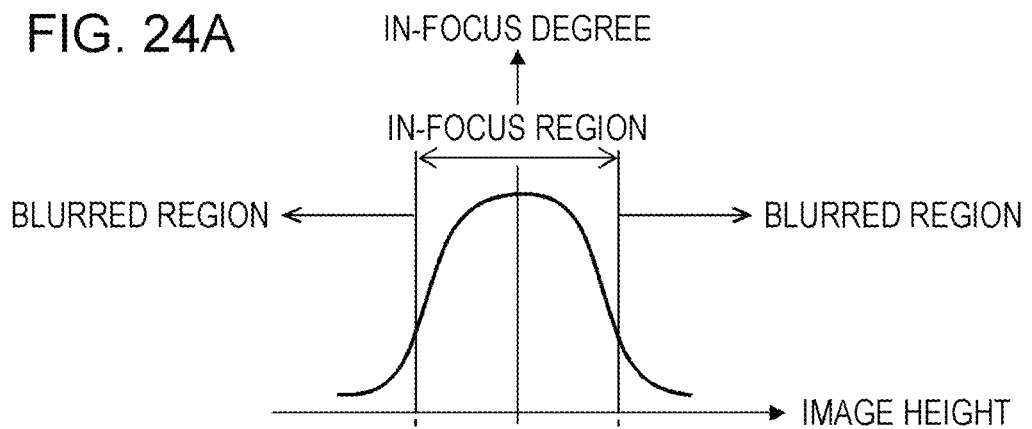
FIGS. 24A to 24C are diagrams illustrating a state where blurring occurs due to curvature of field.
Figure 24B:
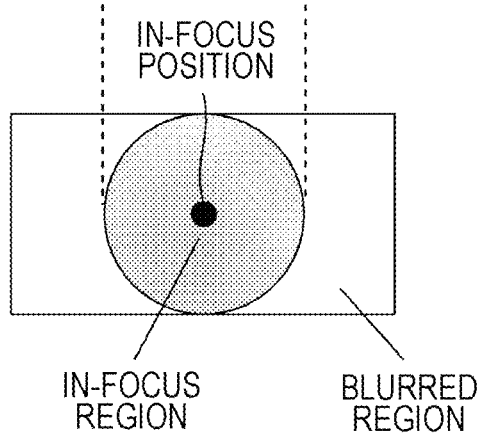
Figure 24C:
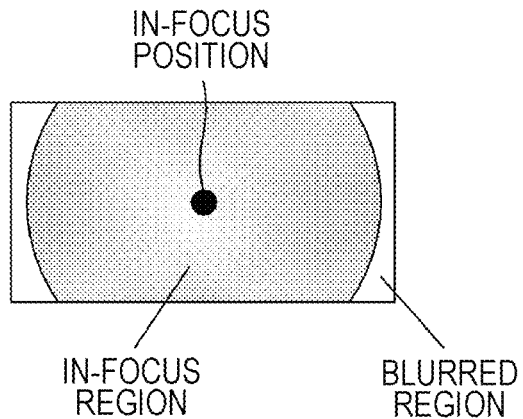
Figure 25A:
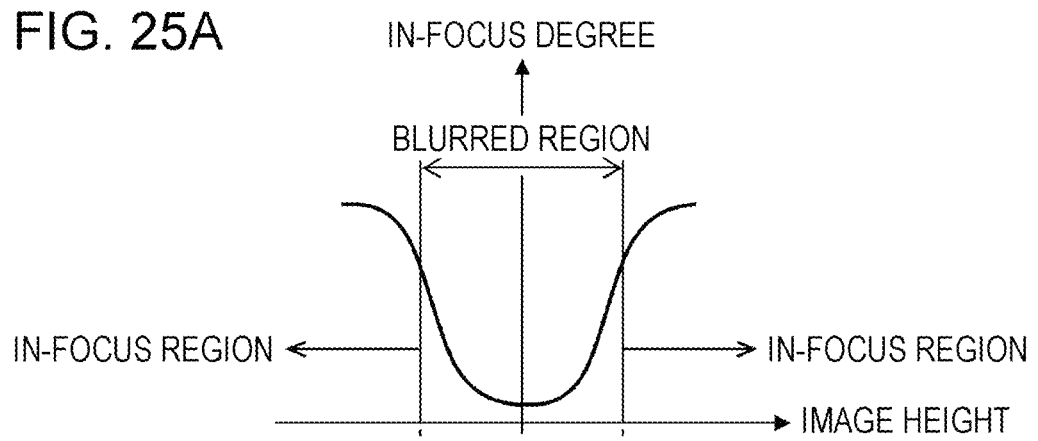
FIGS. 25A and 25B are other diagrams illustrating a state where blurring occurs due to curvature of field.
Figure 25B:
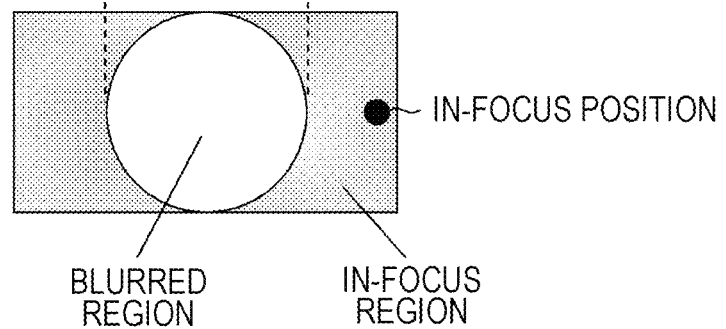

In a case where curvature of field is present due to the characteristics of the imaging optical system, when the center part of an image is in focus, the peripheral part is blurred, and when the peripheral part is in focus, the center part is blurred. For example, in a case where the center part of an image is in focus (the in-focus degree is high) as illustrated in FIG. 24A, the peripheral part of the image is blurred (the in-focus degree is low) as illustrated in FIG. 24B. In a case where the peripheral part of an image is in focus as illustrated in FIG. 25A, the center part of the image is blurred as illustrated in FIG. 25B. The display control unit 210D can display the in-focus region and/or the blurred region (check target region) in a distinguishable manner, and the image determination unit 210C can determine an image that includes a blurred region (check target region) to be a check target image. Distinguishable display can be performed by adding different characters, numerals, figures, symbols, colors, etc. to the in-focus region and the blurred region or changing the degrees thereof. Distinguishable display may be applied to any one of the regions (for example, the in-focus region may be grayed out), or distinguishable display may be applied to both regions. Accordingly, the user can easily distinguish a region (blurred region) in which erroneous detection, omission in detection, etc. is likely to occur, and can efficiently check and/or revise the results of damage detection. Note that the in-focus region may have a shape as illustrated in FIG. 24C depending on the characteristics of the imaging optical system. Therefore, it is preferable to store in advance the relationship between the in-focus position and the in-focus area in the storage unit 220 as a database.

Determination Based on Flashing of Strobe Light

Figure 26A:
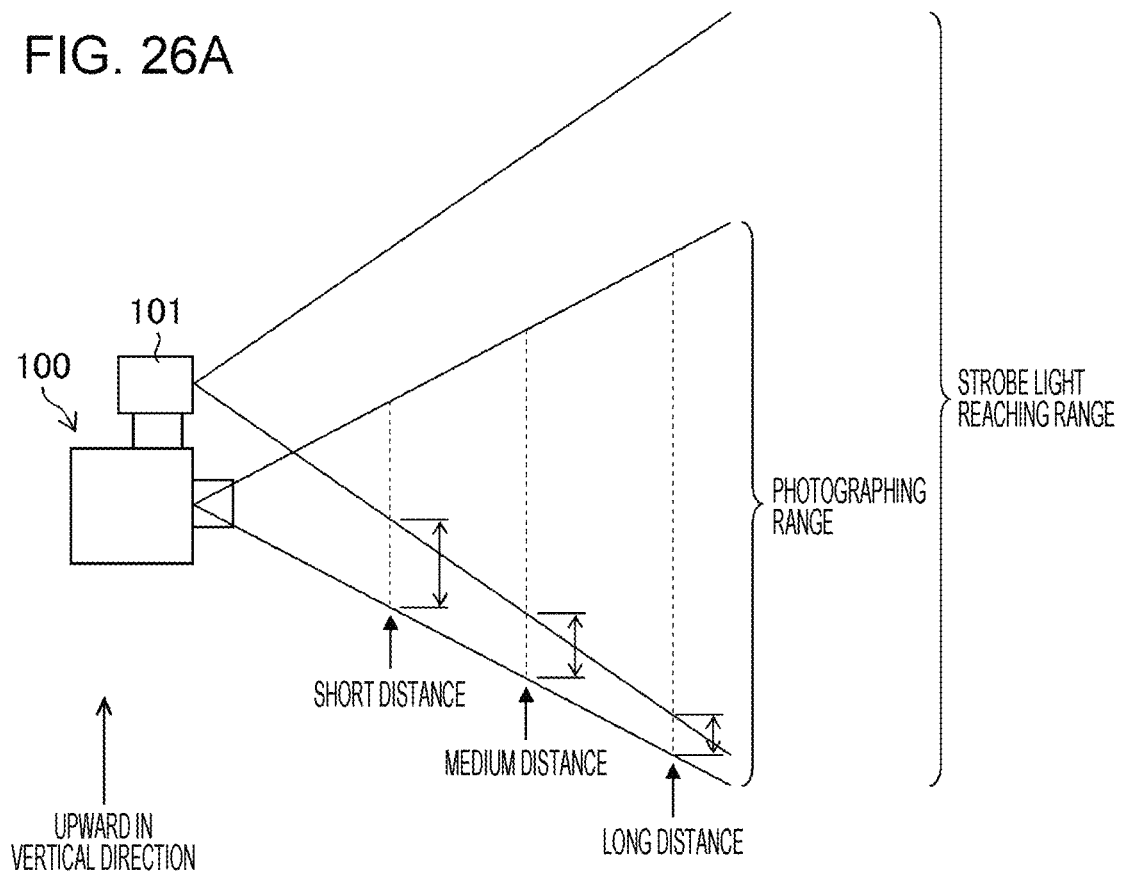
FIGS. 26A and 26B are diagrams illustrating a state of photographing using a stroboscope device.
Figure 26B:
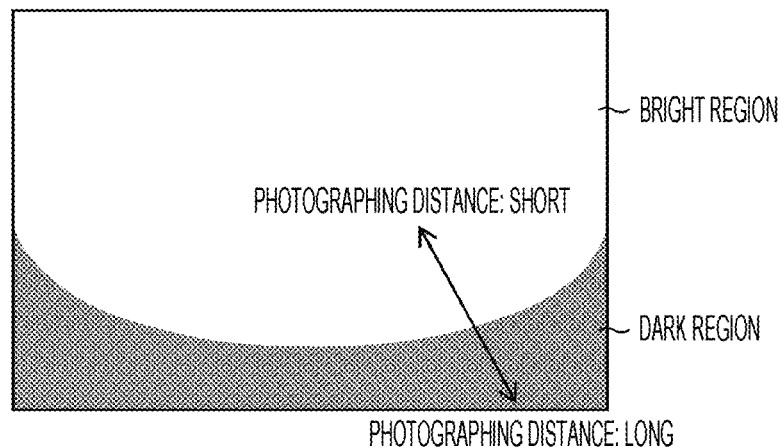

In a case of photographing using strobe light, part of the image becomes dark (the luminance decreases) depending on conditions including the brightness of the strobe light, the photographing area, etc., and omission in detection and/or erroneous detection is likely to occur. Therefore, it is preferable to regard a dark region as a check target. For example, as illustrated in FIG. 26A, in a case where a stroboscope device 101 is mounted on the upper part of the digital camera 100 to carry out photographing, the luminance in the captured image changes as illustrated in FIGS. 26A and 26B (the lower side of the image is likely to become darker) due to the arrangement of the stroboscope device (the light source of the strobe light) and the imaging optical system. As the photographing distance is shorter, the dark region increases, and as the photographing distance is longer, the dark region decreases. Accordingly, it is preferable to set and store in the storage unit 220 the low-luminance region based on the photographing distance. The display control unit 210D can display the bright region (high-luminance region) and/or the dark region (low-luminance region) in a distinguishable manner, and the image determination unit 210C can determine an image that includes the dark region to be a check target image. Distinguishable display can be performed by adding different characters, numerals, figures, symbols, colors, etc. to the bright region and the dark region or changing the degrees thereof. Distinguishable display may be applied to any one of the regions (for example, the bright region may be grayed out), or distinguishable display may be applied to both regions. Accordingly, the user can easily distinguish a region (dark region) in which erroneous detection, omission in detection, etc. is likely to occur, and can efficiently check and revise the results of damage detection.

Determination Based on Construction of Photographic Subject

Figure 28:
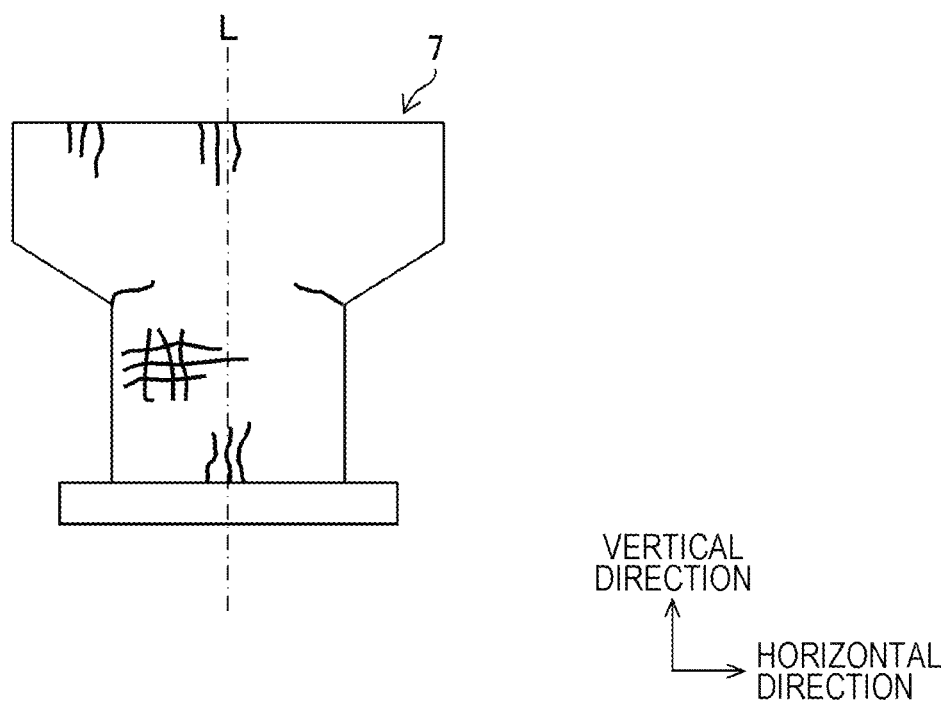
FIG. 28 is a diagram illustrating a state where cracks appear in a pier.

Depending on the construction of a photographic subject, a location where damage is likely to occur is present. For example, in a case of each panel of the floor slab 6, cracks are likely to appear in the center part as illustrated in FIGS. 27A to 27E (FIGS. 27A to 27E are diagrams illustrating an example situation of the appearance of cracks in one panel of the floor slab 6 in a chronological manner). In a case of the pier 7, as illustrated in FIG. 28, cracks are likely to appear near a center axis L in the horizontal direction, near the middle part between the center axis L and the end part, a part in which the shape changes, etc. The display control unit 210D can display a region in which cracks are less likely to appear (for example, a region i20 in FIG. 27C) in a distinguishable manner, and the image determination unit 210C can determine an image that includes a region (region i21) in which cracks are likely to appear to be a check target image. The display control unit 210D can perform distinguishable display by adding different characters, numerals, figures, symbols, colors, etc. to the region in which cracks are likely to appear and the region in which cracks are less likely to appear or changing the degrees thereof. Distinguishable display may be applied to any one of the regions (for example, the region in which cracks are less likely to appear may be grayed out), or distinguishable display may be applied to both regions.

The likelihood of the appearance of cracks (damage) depends on the construction of the photographic subject, and therefore, it is preferable to acquire construction information (construction information 220D) indicating the construction of the photographic subject and store the construction information in the storage unit 220 for reference at the time of processing. Accordingly, the user can easily distinguish a region in which erroneous detection, omission in detection, etc. is likely to occur, and can efficiently check and/or revise the results of damage detection.

Second Embodiment

Configuration of Image Processing Apparatus

Figure 29:
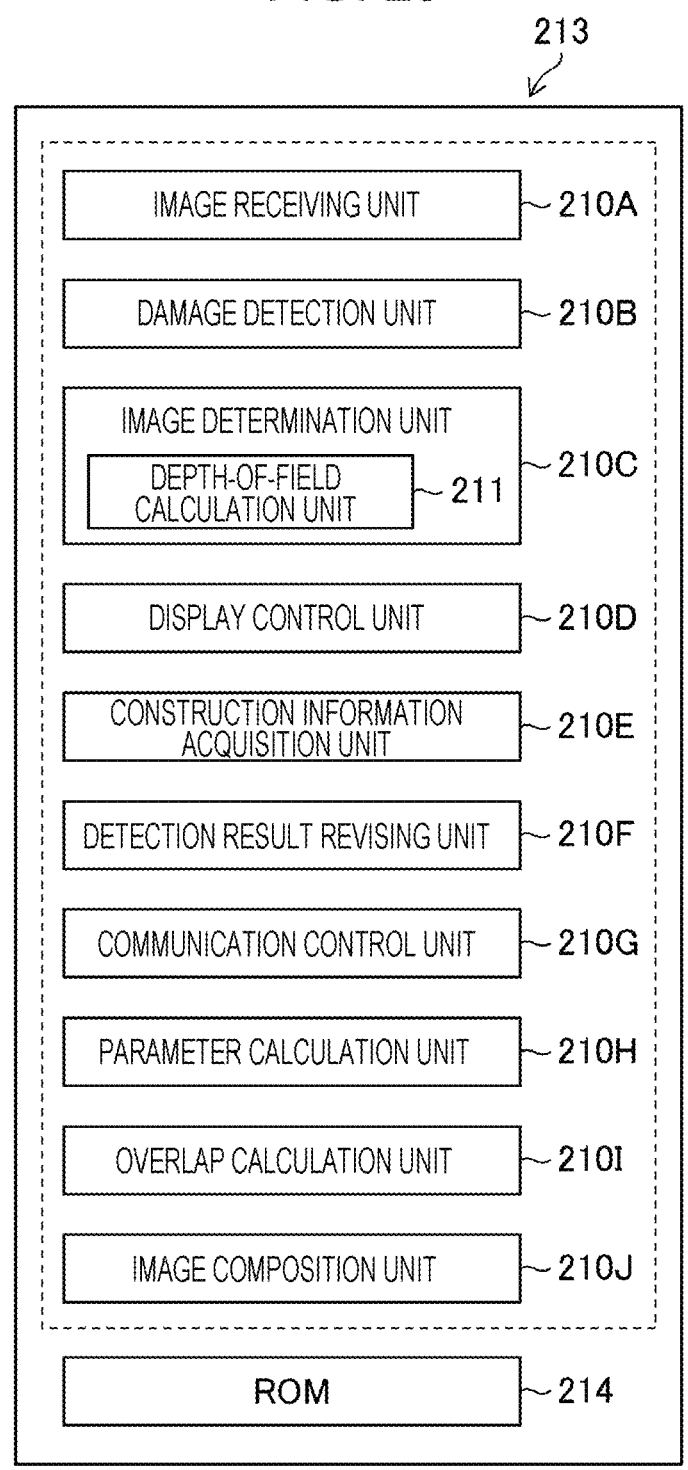
FIG. 29 is a diagram illustrating a configuration of a processing unit according to a second embodiment.

A second embodiment of the image processing apparatus and the image processing method according to the present invention will be described. The second embodiment is different from the first embodiment in that composition parameters for a plurality of individual images are calculated for use in processing. FIG. 29 is a diagram illustrating a configuration of a processing unit (processing unit 213) of the image processing apparatus according to the second embodiment. The processing unit 213 further includes a parameter calculation unit 210H (parameter calculation unit), an overlap calculation unit 210I (overlap calculation unit), and an image composition unit 210J (image composition unit) in addition to the elements of the processing unit 210 illustrated in FIG. 3. Similarly to the elements illustrated in FIG. 3, the functions of the parameter calculation unit 210H, the overlap calculation unit 210I, and the image composition unit 210J can be implemented by using various processors. Note that the other elements of the image processing apparatus are the same as those in the first embodiment, and therefore, the same elements are referenced by the same numerals, and duplicated descriptions thereof will be omitted.

Information Stored in Storage Unit

Figure 30:
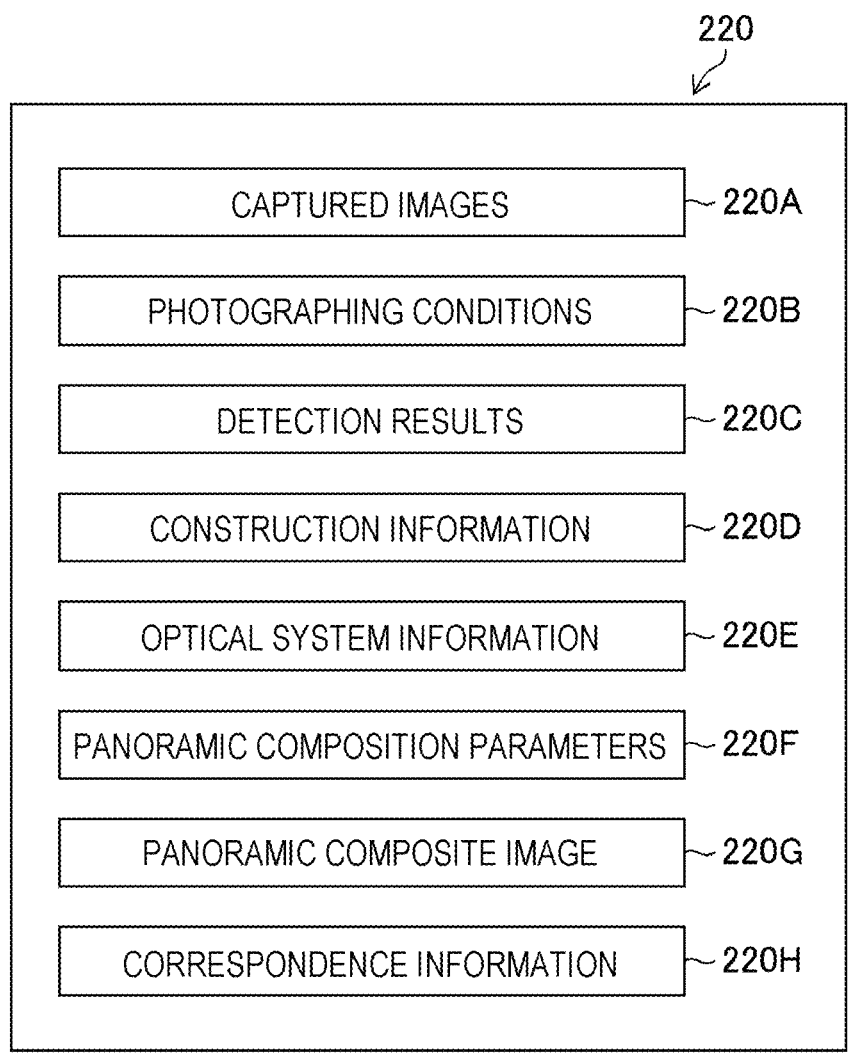
FIG. 30 is a diagram illustrating information stored in a storage unit according to the second embodiment.

FIG. 30 is a diagram illustrating information stored in the storage unit 220 in the second embodiment. In the second embodiment, panoramic composition parameters 220F, a panoramic composite image 220G, and correspondence information 220H are stored in addition to the information stored in the first embodiment.

Procedure for Image Processing

Figure 31:
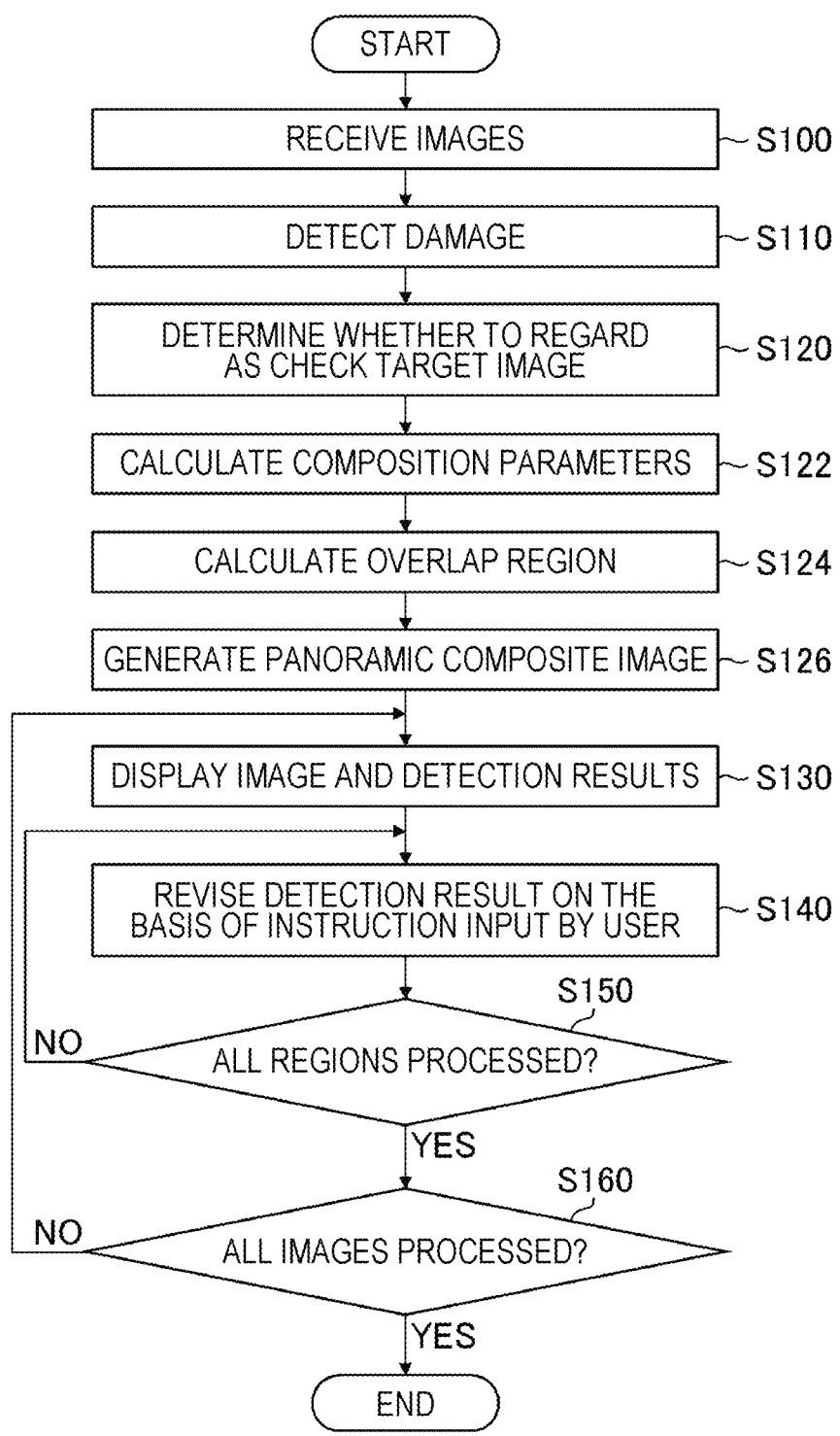
FIG. 31 is a flowchart illustrating a process in an image processing method according to the second embodiment.

The procedure for image processing (image processing method) in the second embodiment is described with reference to the flowchart in FIG. 31. Steps in which a process the same as that in the first embodiment is performed are assigned the same reference numerals, and detailed descriptions thereof will be omitted.

Calculation of Composition Parameters and Generation of Panoramic Composite Image The parameter calculation unit 210H calculates composition parameters (parameters indicating movement, rotation, and modification of the images in a case of composition) by obtaining a projective transformation matrix from correspondence points in the images (step S122: parameter calculation step). The overlap calculation unit 210I obtains an overlap region between the images (plurality of individual images) on the basis of the composition parameters (step S124: overlap region calculation step), and the image composition unit 210J generates a panoramic composite image from the captured images (plurality of images) on the basis of the composition parameters (step S126: image composition step). The image composition unit 210J calculates information indicating the correspondence between the panoramic composite image and the captured images (plurality of images) (information indicating each captured image and a corresponding part of the panoramic composite image, namely, correspondence information). The composition parameters calculated in step S122 are stored in the storage unit 220 as the panoramic composition parameters 220F, the panoramic composite image (for example, a panoramic composite image i30 illustrated in FIG. 32) generated in step S126 is stored in the storage unit 220 as the panoramic composite image 220G, and the correspondence information is stored in the storage unit 220 as the correspondence information 220H (see FIG. 30).

Figure 32:
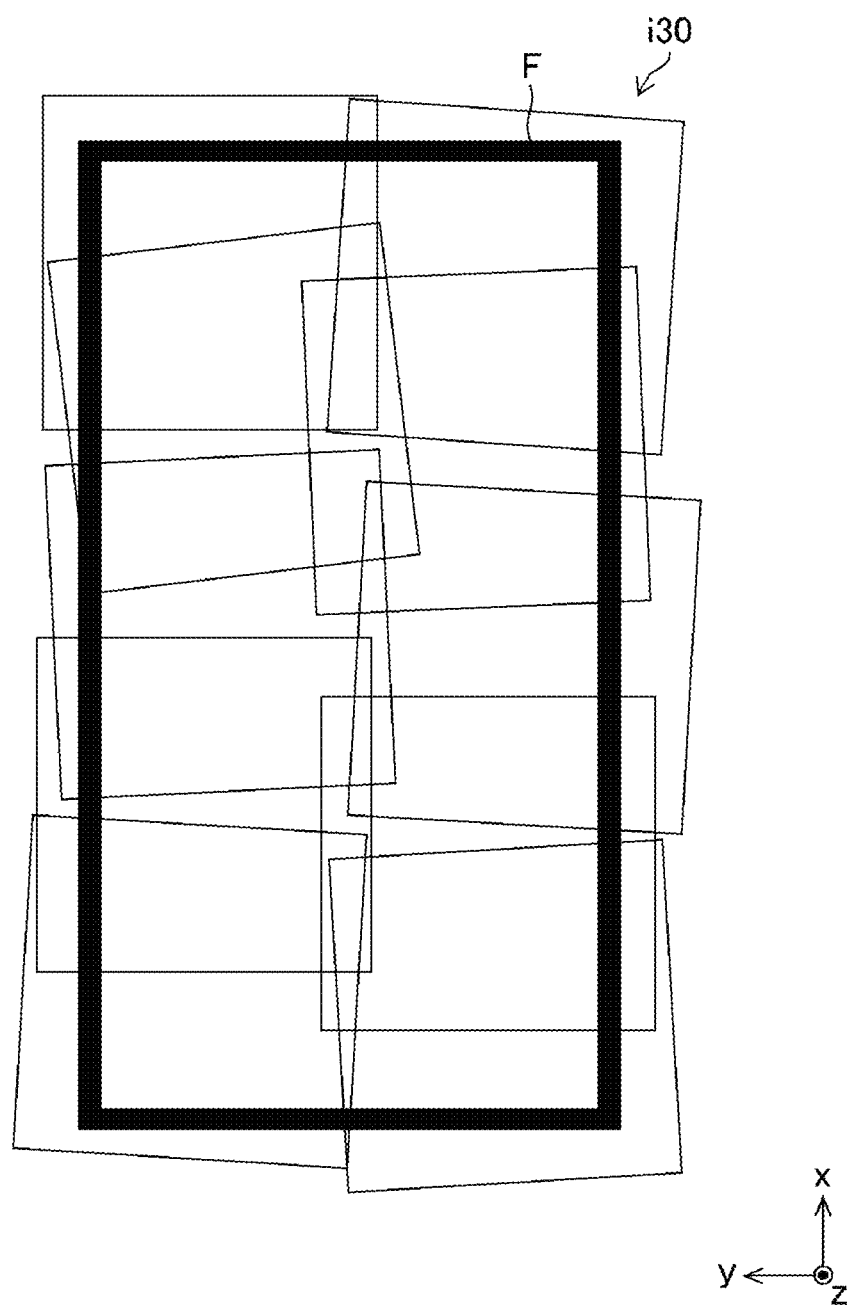
FIG. 32 is a diagram illustrating an example panoramic composite image.

FIG. 32 is a diagram illustrating a state where the panoramic composite image i30 (panoramic composite image) is generated from the images i1 to i10 illustrated in FIG. 8 (the frame F of the panel is illustrated but damage is not illustrated). Note that detection results are checked on a check target image or a partial image, and this image is displayed without reduction. Therefore, in a case of displaying the panoramic composite image, the panoramic composite image may be reduced as necessary (the same as in the case of displaying the entire captured image described in the first embodiment).

Detection of Damage, Check/Revision of Detection Results, Etc.

Figure 33:
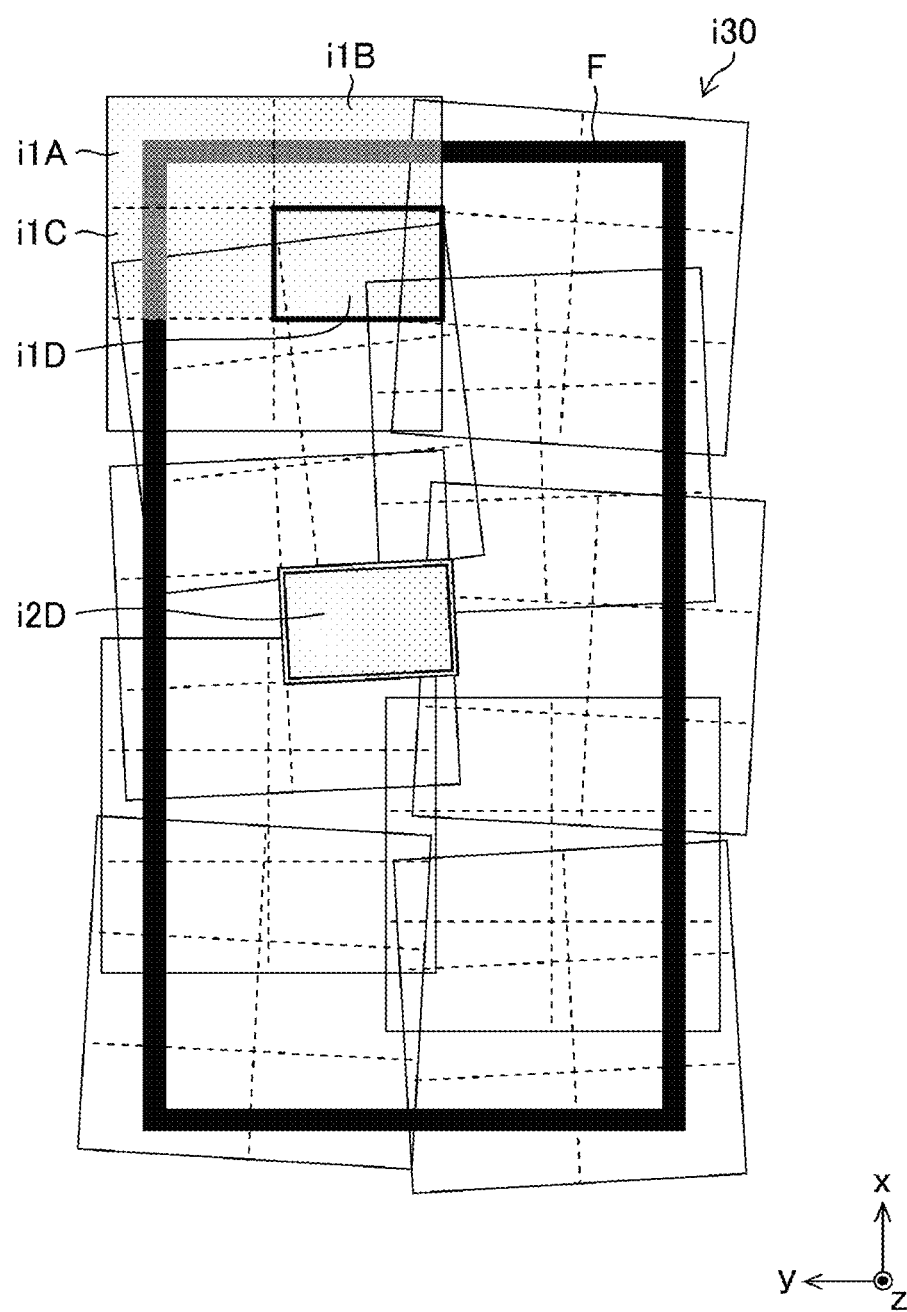
FIG. 33 is a diagram illustrating a state of distinguishable display and specification of an image in a panoramic composite image.

Also in the second embodiment, damage can be detected and detection results can be checked and/or revised as in the first embodiment described above. For a panoramic composite image, such as the panoramic composite image i30, the image and/or the detection results can be displayed in a distinguishable manner as in the first embodiment. FIG. 33 is a diagram illustrating a state where the display control unit 210D displays regions for which checking and/or revision of detection results are completed (the partial images i1A to i1C) and a region that is currently checked (the partial image i1D) in the panoramic composite image i30 in a distinguishable manner. FIG. 33 is a diagram corresponding to FIG. 15C in the first embodiment. When the user specifies a desired region (for example, the area of a partial image i2D) in the panoramic composite image i30, the display control unit 210D displays an image corresponding to the specified area and the detection results in the image on the monitor 232 as illustrated in FIG. 14 on the basis of the correspondence information (correspondence information 220H). With such display, also in the second embodiment, the user can easily grasp regions for which checking and/or revision of detection results are completed, and can efficiently check and revise detection results.

Distinguishable Display of Overlap Region

In a case of acquiring a plurality of images by photographing a photographic subject in sections, an overlap region in which a plurality of images overlap appears depending on overlapping of the photographing areas. In a case of checking and/or revising detection results for each image in such a situation, the user is to check detection results several times for the overlap region, and the operation becomes inefficient. In the overlap region, the image quality differs among the images depending on the photographing conditions, and the precision of damage detection differs accordingly. Therefore, the user may check and/or revise detection results on an image having low image quality (low detection precision). Such a problem becomes significant in a case where the inspection area is wide and a large number of images are acquired. Accordingly, in the second embodiment, an overlap region is displayed in a distinguishable manner as described below (step S130).

Figure 34A:
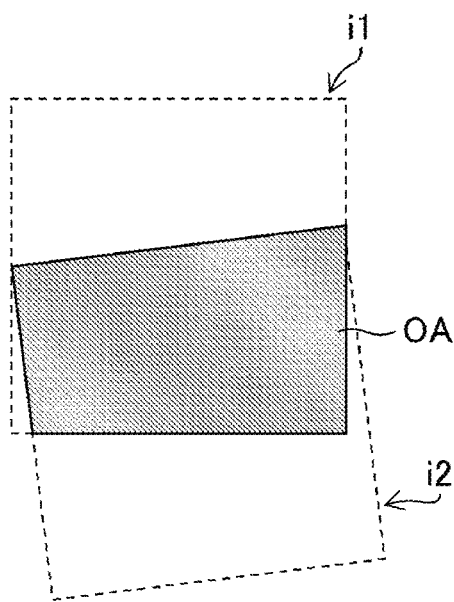
FIGS. 34A and 34B are diagrams illustrating example distinguishable display of an overlap region.
Figure 34B:
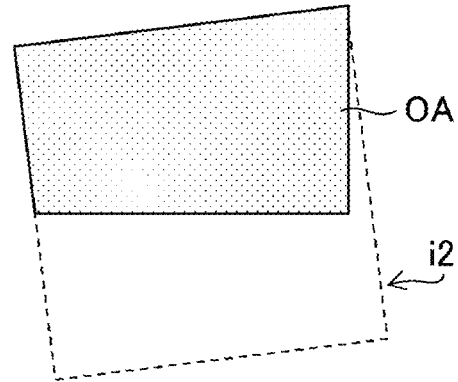

Specifically, in a case where a processing target overlap region has been checked in any image or in a case where a processing target overlap region is other than an overlap region having the highest image quality, the display control unit 210D displays the processing target overlap region in a distinguishable manner. FIGS. 34A and 34B are diagrams illustrating an example of such distinguishable display, and FIG. 34A illustrates a state where an overlap region OA in which the image i1 and the image i2 overlap is present. In a case where detection results in the overlap region OA are checked on the image i1 in this state or in a case where the image quality of the overlap region OA in the image i1 is higher than the image quality of the overlap region OA in the image i2 (that is, the overlap region OA in the image i2 is other than an overlap region having the highest image quality), the display control unit 210D grays out the overlap region OA (an example of distinguishable display) when displaying the image i2 (see FIG. 34B). Distinguishable display may be performed by adding a character, a figure, or a symbol or by coloration, etc. instead of gray-out display. With such distinguishable display, the user can easily grasp that the overlap region displayed in a distinguishable manner has no need for checking (or a reduced need for checking), and can efficiently check and revise detection results. The need for checking can be grasped with distinguishable display of the overlap region, and therefore, the display control unit 210D need not display detection results in a distinguishable manner. Alternatively, the overlap region need not be "displayed in a distinguishable manner", and display of the overlap region may be skipped.

Note that determination as to "whether an overlap region has been checked in any image" can be performed by, for example, the detection result revising unit 210F adding a flag to a "check completed" detection result and the display control unit 210D referring to this flag (see FIGS. 9A and 9B). Determination as to whether "an overlap region is other than an overlap region having the highest image quality" can be performed by, for example, the image determination unit 210C calculating and converting the image quality to a numerical value using the technique described above in the first embodiment and associating the numerical value of the image quality value with a detection result (for example, providing a column "image quality" in the table illustrated in FIGS. 9A and 9B) and the display control unit 210D comparing the image quality between images. Note that as long as the composition parameters can be calculated, an overlap region can be displayed in a distinguishable manner. Therefore, a panoramic composite image needs to be generated and stored when necessary (for example, in a case where the user wants to check, on a panoramic image, an area occupied by an image that is being displayed).

The embodiments of the present invention have been described above; however, the present invention is not limited to the above-described forms, and various modifications can be made without departing the spirit of the present invention.

REFERENCE SIGNS LIST 1 bridge
2 main girder
3 cross girder
4 sway bracing
5 lateral bracing
6 floor slab
7 pier
10 image processing apparatus
100 digital camera
101 stroboscope device
110 image capturing unit
130 wireless communication unit
132 antenna
200 image processing apparatus main body
210 processing unit
210A image receiving unit
210B damage detection unit
210C image determination unit
210D display control unit
210E construction information acquisition unit
210F detection result revising unit
210G communication control unit
210H parameter calculation unit
210I overlap calculation unit
210J image composition unit
211 depth-of-field calculation unit
212 antenna
213 processing unit
214 ROM
220 storage unit
220A captured images
220B photographing conditions
220C detection results
220D construction information
220E optical system information
220F panoramic composition parameters
220G panoramic composite image
220H correspondence information
230 display unit
232 monitor
240 operation unit
242 keyboard
244 mouse
A region
A1 region
Ai region
Aj region
An region
F frame
G0 panel
i1 image
i2 image
i3 image
i4 image
i5 image
i6 image
i7 image
i8 image
i9 image
i10 image
i1A partial image
i1B partial image
i1C partial image
i1D partial image
i1E partial image
i1F partial image
i20 region
i21 region
i2D partial image
i30 panoramic composite image
iA image
iB image
iC image
L center axis
OA overlap region
S100 to S160 steps in image processing method

What is claimed is:

1. An image processing apparatus comprising:
one or more processors and a non-transitory, tangible recording medium, wherein the one or more processors are configured to perform:
receiving a plurality of images acquired by an image capturing unit including an imaging optical system and an imaging element configured for photographing a photographic subject in sections, the photographic subject being an architectural or civil structure;
detecting damage to the photographic subject from individual images that are images individually forming the plurality of images;
determining whether each individual image among the individual images is to be regarded as a check target image for encouraging a user to check a detection result for the individual image;
controlling display of the plurality of images and the detection result on a display device; and
revising the detection result on the basis of an instruction input by the user,
wherein the one or more processors are further configured to perform:
controlling display, on the display device, of an image that is determined to be the check target image among the plurality of images and the detection result associated with the check target image, and another image that is determined to be the check target image among the plurality of images and the detection result associated with the check target image according to an instruction input for switching the display, or controlling display, on the display device, of an image among the plurality of images and the detection result associated with the image, another image among the plurality of images and the detection result associated with the another image according to an instruction input for switching the display, and an image that is determined to be the check target image so as to be distinguishable from an image that is determined to be a non-check target image.

2. The image processing apparatus according to claim 1, wherein the one or more processors are further configured to perform:

determining the check target image on the basis of at least one of image quality of the individual image, the detection result, a photographing condition, or a construction of the photographic subject.

3. The image processing apparatus according to claim 2, wherein the one or more processors are further configured to perform:

obtaining the image quality on the basis of at least one of a result of evaluation by an image quality evaluator configured by machine learning, a spatial frequency spectrum of the individual image, or a density histogram of the individual image.

4. The image processing apparatus according to claim 1, wherein the one or more processors are further configured to perform:

determining the check target image on the basis of the number and/or density of detection results, in the individual image, for each of which a degree of certainty indicating actual damage is equal to or larger than a threshold.

5. The image processing apparatus according to claim 4, wherein the one or more processors are further configured to perform:

controlling display, on the display device, of each detection result in a distinguishable manner in accordance with the degree of certainty.

6. The image processing apparatus according to claim 4, wherein the one or more processors are further configured to perform:

controlling display, on the display in a distinguishable manner, of a region, in the check target image, in which a detection result for which the degree of certainty is equal to or larger than the threshold is present.

7. The image processing apparatus according to claim 1, wherein the one or more processors are further configured to perform:

calculating a depth of field of each individual image, and in a case where the individual image includes a region outside a range of the depth of field, determining that the individual image is to be regarded as the check target image.

8. The image processing apparatus according to claim 7, wherein the one or more processors are further configured to perform:

calculating the depth of field on the basis of a photographing angle of the photographic subject in the check target image and an in-focus position in the check target image.

9. The image processing apparatus according to claim 7, wherein the one or more processors are further configured to perform:

calculating the depth of field on the basis of a photographing angle of the photographic subject, a photographing distance to the photographic subject, an aperture value used when the check target image is captured, and a permissible circle of confusion diameter.

10. The image processing apparatus according to claim 7, wherein the one or more processors are further configured to perform:

controlling display, on the display in a distinguishable manner, of a region, in the check target image, outside the range of the depth of field.

11. The image processing apparatus according to claim 7, wherein the one or more processors are further configured to perform:

controlling display, on the display in a distinguishable manner, of a check target region, in the check target image, set in accordance with curvature of field of the imaging optical system and an in-focus position.

12. The image processing apparatus according to claim 1, wherein in a case where the individual image is captured while strobe light is flashed and where the individual image includes a low-luminance region that is set in accordance with a change in luminance caused by an arrangement of a light source of the strobe light and the imaging optical system, the one or more processors are further configured to perform determining that the individual image is to be regarded as the check target image.

13. The image processing apparatus according to claim 12, wherein the low-luminance region is a region set on the basis of a photographing distance.

14. The image processing apparatus according to claim 12, wherein the one or more processors are further configured to perform:

controlling display, on the display in a distinguishable manner, of the low-luminance region in the check target image.

15. The image processing apparatus according to claim 1, wherein the one or more processors are further configured to perform:

acquiring construction information indicating a construction of the photographic subject, and in a case of determining with reference to the construction information that a photographing area of the individual image includes a region in which damage is likely to occur, determining that the individual image is to be regarded as the check target image.

16. The image processing apparatus according to claim 1, wherein the one or more processors are further configured to perform:

calculating a parameter for performing panoramic composition of the plurality of images; and calculating an overlap region between the plurality of individual images on the basis of the parameter, wherein in a case where the overlap region has been checked in any image or in a case where the overlap region is other than a region having highest image quality, the one or more processors are further configured to perform controlling display, on the display, of the overlap region in a distinguishable manner.

17. The image processing apparatus according to claim 16, wherein the one or more processors are further configured to perform:
generating a panoramic composite image from the plurality of images on the basis of the parameter, and
controlling display, on the display in a distinguishable manner, of an area, in the panoramic composite image, represented by the check target image.

18. The image processing apparatus according to claim 17, wherein the one or more processors are further configured to perform:
controlling display, on the display in a distinguishable manner, of an area that has been checked and/or revised in the panoramic composite image.

19. The image processing apparatus according to claim 17, wherein the one or more processors are further configured to perform:
calculating information indicating a correspondence between the panoramic composite image and the plurality of images, and
controlling display, on the display, of an image, among the plurality of images, corresponding to an area specified in the panoramic composite image on the basis of the information.

20. The image processing apparatus according to claim 1, wherein
the image capturing unit comprises a digital camera configured to capture an image of the photographic subject with the imaging optical system and the imaging element on which an optical image of the photographic subject is formed by the imaging optical system.

21. The image processing apparatus according to claim 1, wherein
the one or more processors are further configured to perform controlling display, on the display device, of an image and results of crack detection in association with each other by at least one of: superimposing and displaying bold lines or rectangles on crack parts including cracks in the image, coloring the bold lines or rectangles, displaying numeric values indicating widths of the cracks, and changing brightness and/or saturation of coloration in accordance with degree of damage.

22. The image processing apparatus according to claim 1, wherein
the revising of the detection result includes at least one revision including addition, correction, or deletion of the detection result.

23. The image processing apparatus according to claim 1, wherein
the one or more processors are further configured to perform identifying a region occupied by a partial image in the entire check target image and controlling display, on the display device, of the region occupied by the partial image in the entire check target image.

24. The image processing apparatus according to claim 1, wherein
the architectural or civil structure is any one of a bridge, a tunnel, a building, and a road.

25. An image processing method comprising:
an image receiving step of receiving a plurality of images acquired by photographing a photographic subject in sections using an imaging optical element and an imaging element, the photographic subject being an architectural or civil structure;
a damage detection step of detecting damage to the photographic subject from individual images that are images individually forming the plurality of images;
an image determination step of determining whether each individual image among the individual images is to be regarded as a check target image for which a user is encouraged to check a detection result for the individual image;
a display control step of controlling display of the plurality of images and the detection result on a display device,
the display control step including:
displaying, on the display device, an image that is determined to be the check target image among the plurality of images and the detection result associated with the check target image, and another image that is determined to be the check target image among the plurality of images and the detection result associated with the another image according to an instruction input for switching the display,
or
displaying, on the display device, an image among the plurality of images and the detection result associated with the image, another image among the plurality of images and the detection result associated with the another image according to an instruction input for switching the display, and an image that is determined to be the check target image so as to be distinguishable from an image that is determined to be a non-check target image; and
a detection result revising step of revising the detection result on the basis of an instruction input by the user.

26. A non-transitory, tangible computer-readable medium having stored thereon computer instructions that, when executed by a computer, cause the computer to:
obtain a plurality of images acquired by photographing a photographic subject in sections using an imaging optical element and an imaging element, the photographic subject being an architectural or civil structure;
detect damage to the photographic subject, from individual images that are images individually forming the plurality of images;
determine whether each individual image among the individual images is to be regarded as a check target image for which a user is encouraged to check a detection result for the individual image;
control to display the plurality of images and the detection result on a display device,
the control to display including
displaying, on the display device, an image that is determined to be the check target image among the plurality of images and the detection result associated with the check target image, and another image that is determined to be the check target image among the plurality of images and the detection result associated with the another image according to an instruction input for switching the display,
or
displaying, on the display device, an image among the plurality of images and the detection result associated with the image, another image among the plurality of images and the detection result associated with the another image according to an instruction input for switching the display, and an image that is determined to be the check target image so as to be distinguishable from an image that is determined to be a non-check target image; and revise the detection result on the basis of an instruction input by the user.

\* \* \* \* \*